US006880386B1

(12) United States Patent
Krotil et al.

(10) Patent No.: US 6,880,386 B1
(45) Date of Patent: Apr. 19, 2005

(54) METHOD AND DEVICE FOR SIMULTANEOUSLY DETERMINING THE ADHESION, FRICTION, AND OTHER MATERIAL PROPERTIES OF A SAMPLE SURFACE

(75) Inventors: Hans-Ulrich Krotil, Neu-Ulm (DE); Thomas Stifter, Illereichen (DE); Othmar Marti, Ulm (DE)

(73) Assignee: Witec Wissenschaftliche Instrumente und Technologie GmbH, Ulm (DE)

( * ) Notice: Subject to any disclaimer, the term of this patent is extended or adjusted under 35 U.S.C. 154(b) by 0 days.

(21) Appl. No.: 09/869,789

(22) PCT Filed: Jan. 4, 2000

(86) PCT No.: PCT/DE00/00003

§ 371 (c)(1),
(2), (4) Date: Jul. 23, 2002

(87) PCT Pub. No.: WO00/40946

PCT Pub. Date: Jul. 13, 2000

(30) Foreign Application Priority Data

Jan. 5, 1999 (DE) .......................................... 199 00 114

(51) Int. Cl.[7] ........................ G01N 13/16; G01N 19/02; G01N 19/04; G01B 11/30; G01B 21/30
(52) U.S. Cl. ......................................................... 73/105
(58) Field of Search ............................. 73/105, 9, 866, 73/801; 250/306–307

(56) References Cited

U.S. PATENT DOCUMENTS

| | | | |
|---|---|---|---|
| 5,444,244 A | 8/1995 | Kirk et al. | |
| 5,477,732 A | 12/1995 | Yasue et al. | ................... 73/105 |
| 5,503,010 A | 4/1996 | Yamanaka | |

(Continued)

FOREIGN PATENT DOCUMENTS

| | | | | |
|---|---|---|---|---|
| DE | 44 37 081 | | 4/1995 | .......... G01N/19/04 |
| DE | 9421715 U1 | * | 7/1996 | ............ H02N/2/04 |
| DE | 19502822 A1 | * | 8/1996 | ............ H01J/37/28 |
| DE | 197000747 A1 | * | 7/1998 | ............ H01J/37/28 |
| DE | 197 28 357 | | 1/1999 | ............ H01J/37/28 |
| EP | 0 611 945 | | 11/1997 | ............ G01B/7/34 |
| EP | 0 896 201 A1 | | 2/1999 | |
| WO | WO 00/40946 | | 7/2000 | |

OTHER PUBLICATIONS

Kazushi Yamonaka et al "Lateral Force Modulation Atomic Force Microscope for Selective Imaging of Friction Forcess" *Japanese J. Apple Phys.* vol. 34, Part t, No. 5B, pp 2879–2882, May 1995.*

(Continued)

*Primary Examiner*—Thomas P. Noland
(74) *Attorney, Agent, or Firm*—Baker & Daniels

(57) ABSTRACT

A process for the location-resolved simultaneous detection of the adhesion and friction as well as possibly of other material properties of a sample surface to be examined by means of a raster probe microscope comprising a raster probe. The raster probe and/or the sample with sample surface are moved until at a point of the sample surface to be examined the raster probe interacts in a determined manner with this surface. The raster probe and/or the sample are subjected to a vertical oscillation, and a first measuring signal characterized by the deformation of the raster probe is recorded. A second measuring signal characterizing the deformation of the raster probe is recorded, wherein the raster probe and/or the sample are subjected to a horizontal and/or vertical oscillation. From these two measuring signals the desired material properties are determined. For the detection of the entire surface area to be examined the raster probe and or the sample are again moved and for the repetition of the measuring process described brought into contact with the sample surface in the above described manner.

10 Claims, 12 Drawing Sheets

U.S. PATENT DOCUMENTS

| | | | |
|---|---|---|---|
| 5,519,212 A | | 5/1996 | Elings et al. |
| 5,646,339 A | | 7/1997 | Bayer et al. .................. 73/105 |
| 5,763,768 A | | 6/1998 | Henderson et al. |
| 5,804,708 A | | 9/1998 | Yamanaka et al. |
| 5,994,820 A | * | 11/1999 | Kleindiek ................... 310/329 |
| 6,051,833 A | * | 4/2000 | Yasutake ................... 250/306 |
| 6,249,000 B1 | * | 6/2001 | Muramatsu et al. ........ 250/306 |

OTHER PUBLICATIONS

Design and calibration of a scanning force microscope for friction, adhesion & contact potential studies D. D. Koleske et al; *Rev. Ser, Int.,* vol. 66, No. 9, pp. 4566–4574 (pp. 4571 & 4572 incomplete), Sep. 1995.*

English language translation of German Patent No. DE 197 28 357 submitted Jan. 2002, not published.

T. Goddenhenrich et al., "A lateral modulation technique for simultaneous friction and topography measurements with the atomic force microscope", Rev. Sci. Instrum. 65 (9), Sep. 1994, pp. 2870–2873.

S. Watanabe et al., "Two–directional dynamic mode force microscopy: Detection of directional force gradient", J. Vac. Sci. Technol. B 12(3), May/Jun. 1994, pp. 1577–1580.

Kazushi Yamanaka et al., "Ultrasonic force microscopy for nanometer resolution subsurface imaging", Appl. Phys. Lett. 64 (2), Jan. 10, 1994, pp. 178–180.

* cited by examiner

Figure 2:
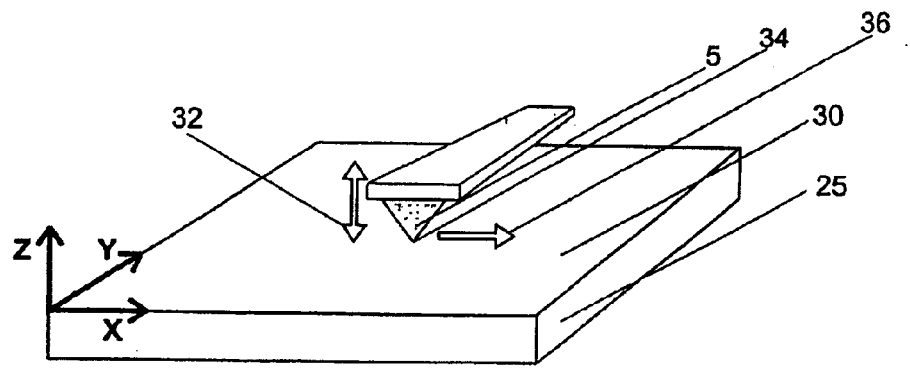
Figure 3A:
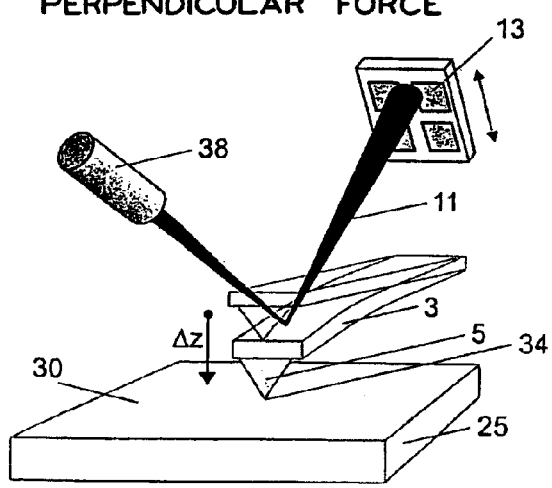
Figure 3B:
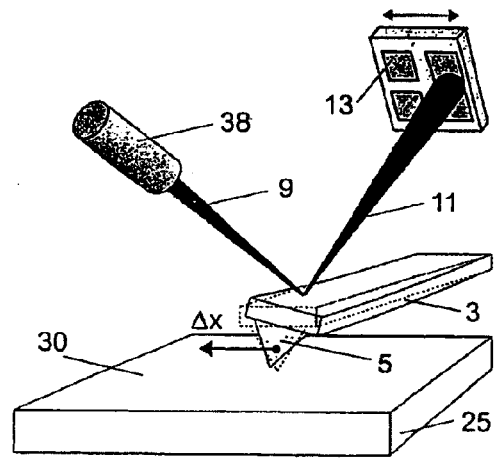
Figure 4A:
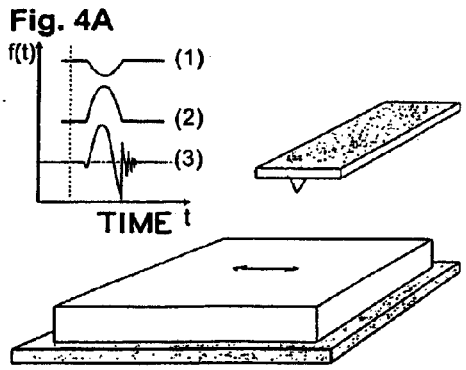
Figure 4B:
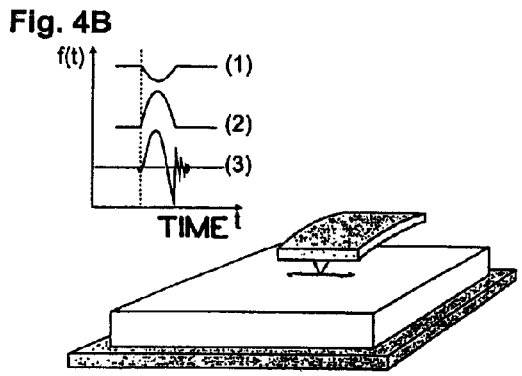
Figure 4C:
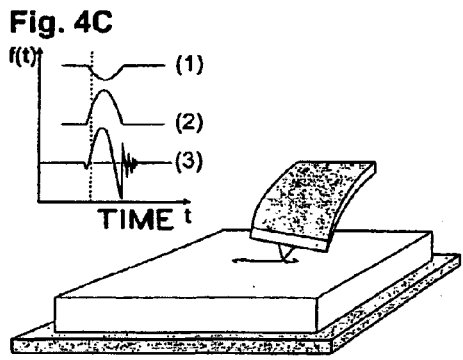
Figure 4D:
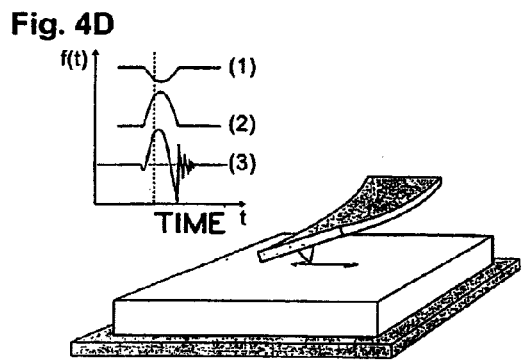
Figure 4E:
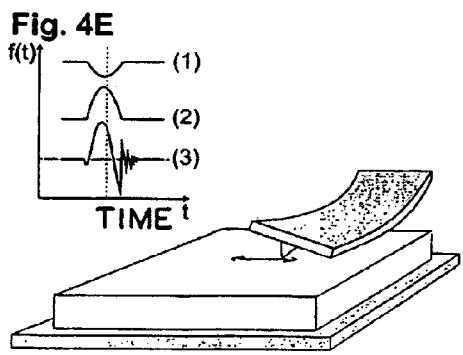
Figure 4F:
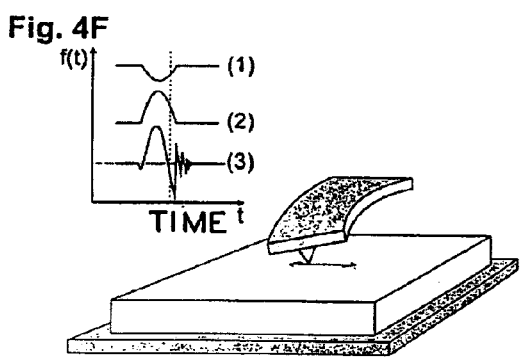
Figure 4G:
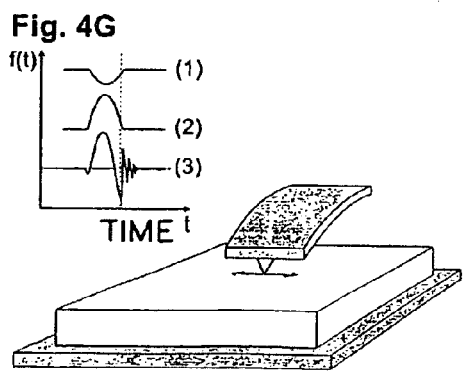
Figure 4H:
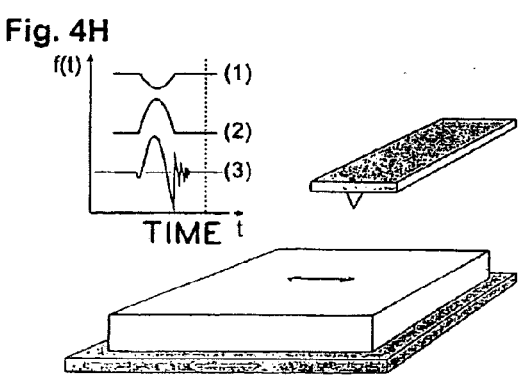
Figure 5:
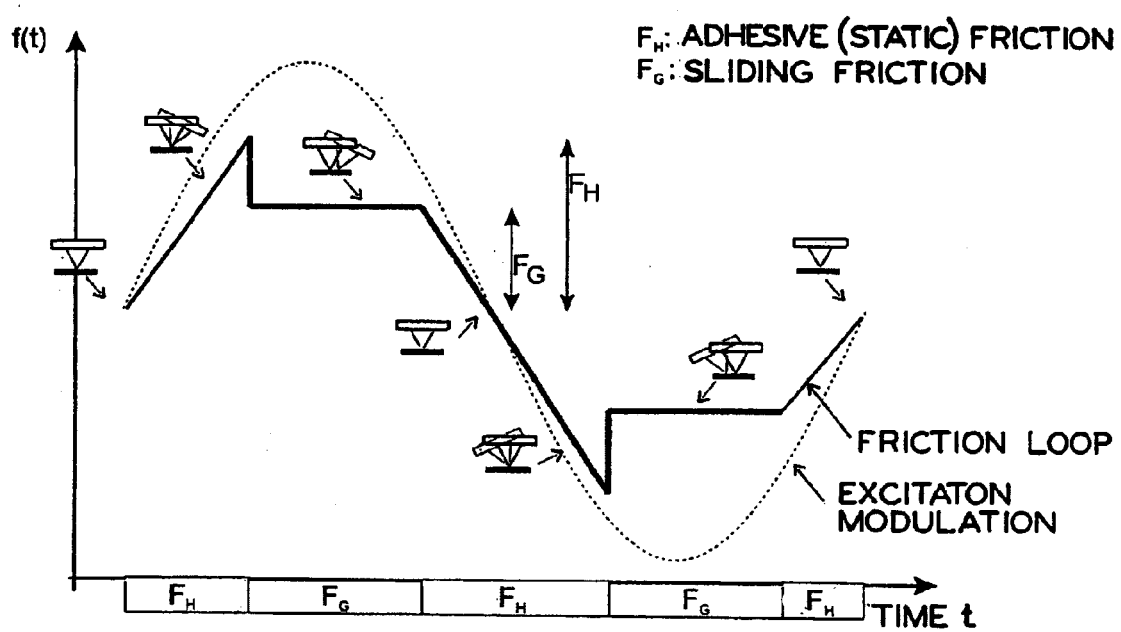
Figure 6:
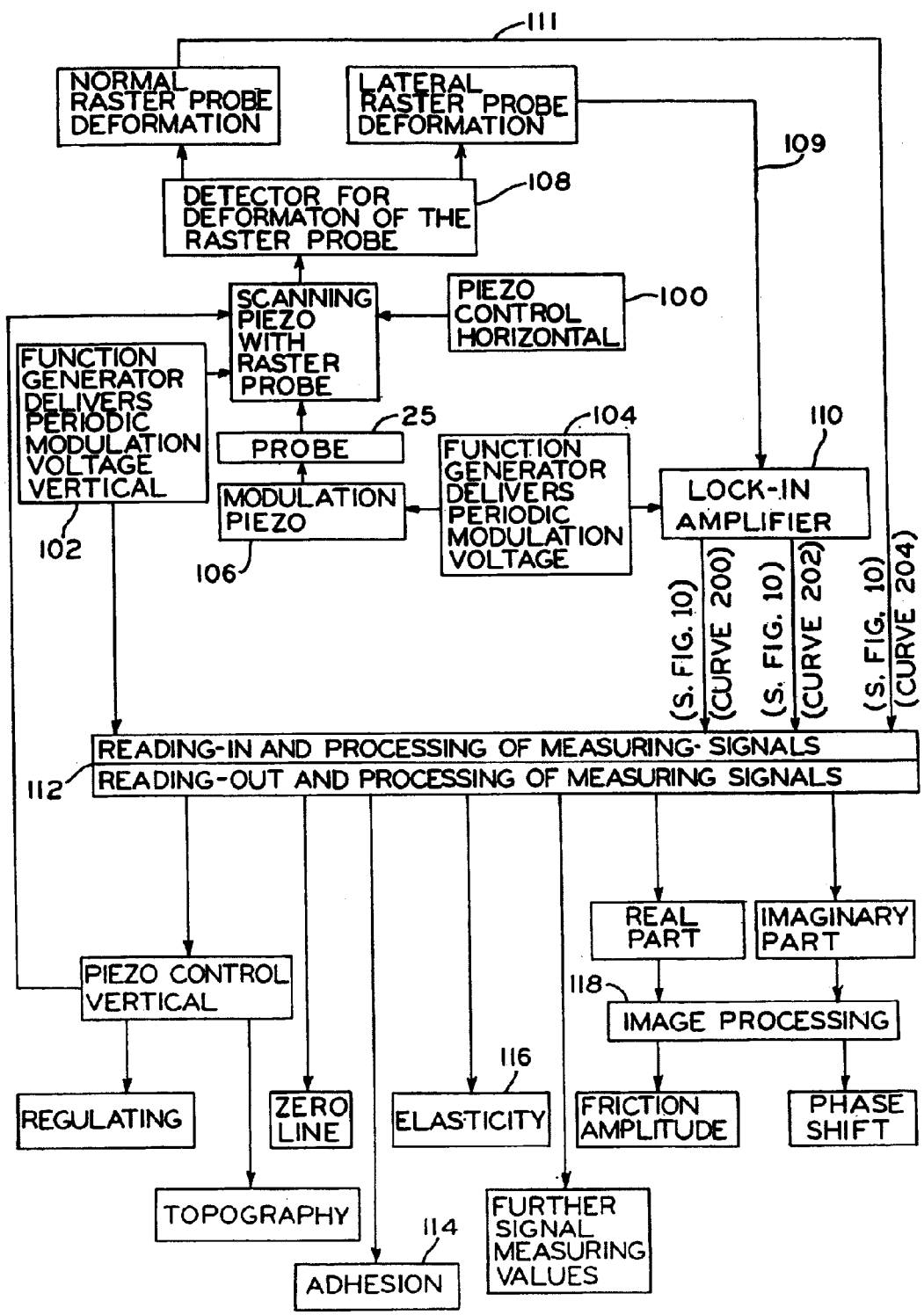
Figure 7A:
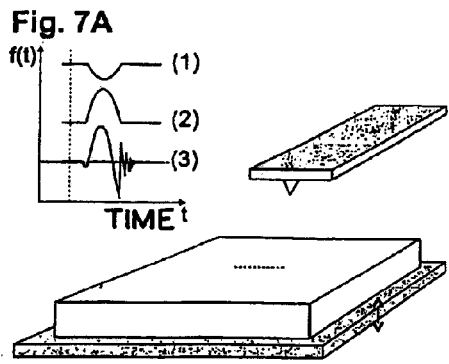
Figure 7B:
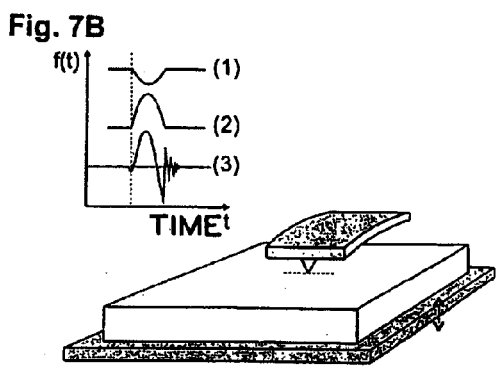
Figure 7C:
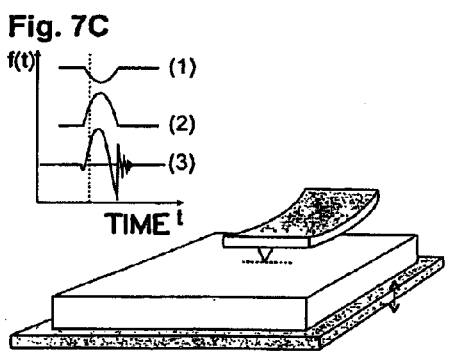
Figure 7D:
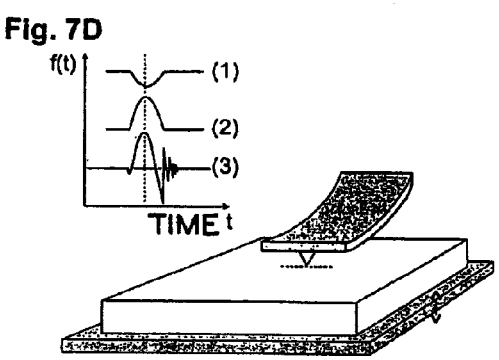
Figure 7E:
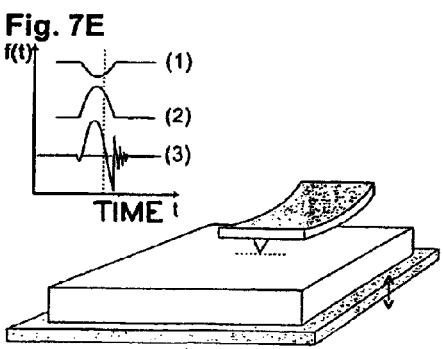
Figure 7F:
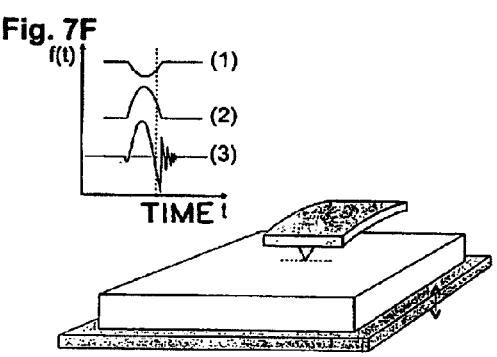
Figure 7G:
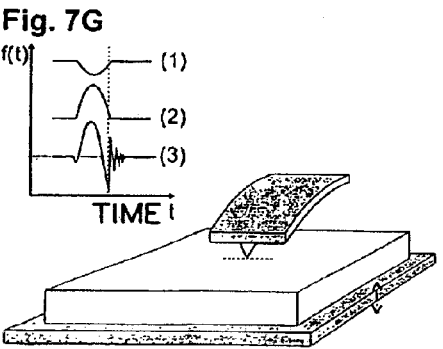
Figure 7H:
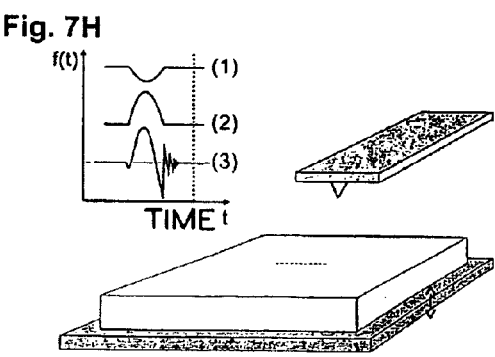
Figure 8:
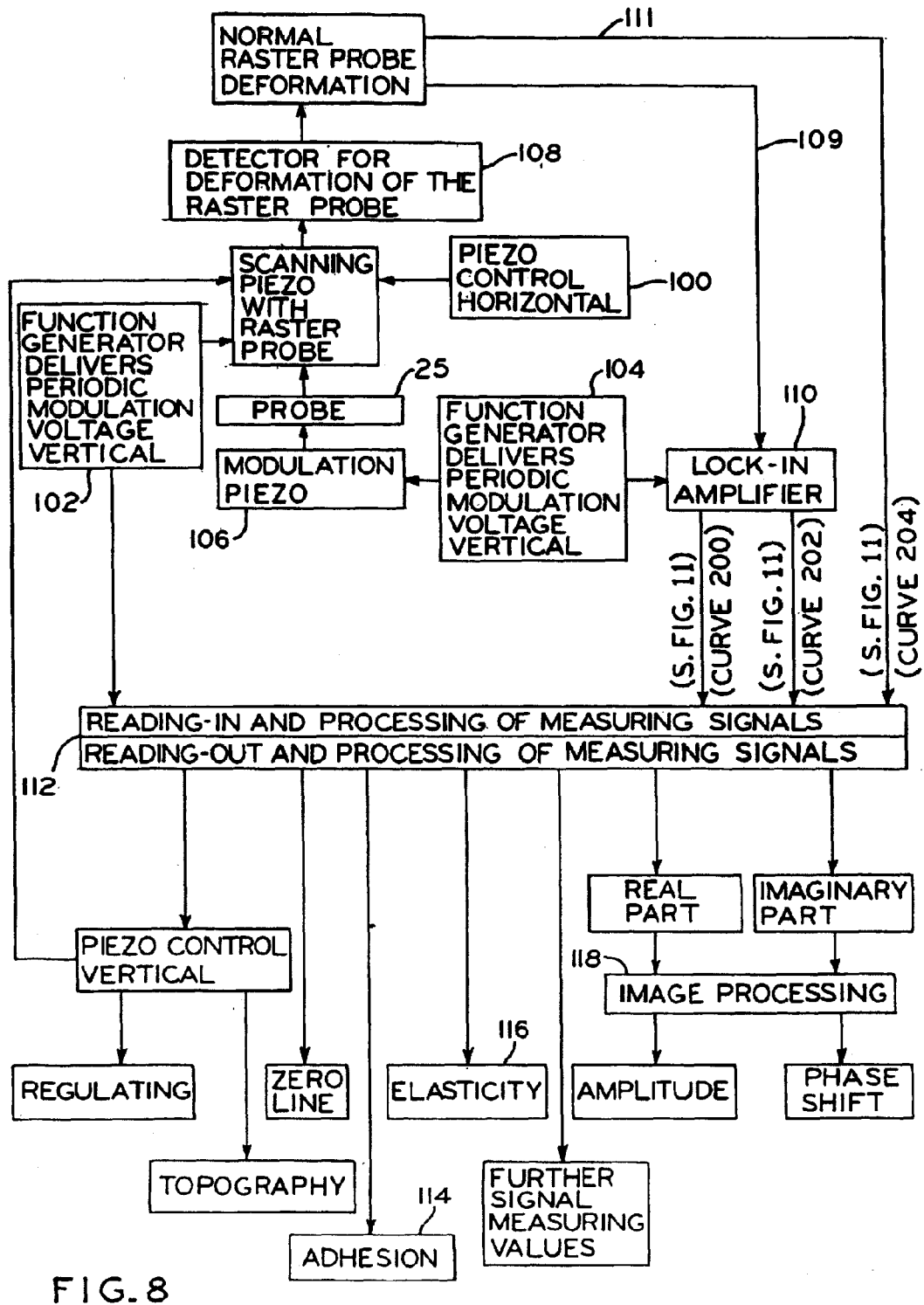
Figure 9A:
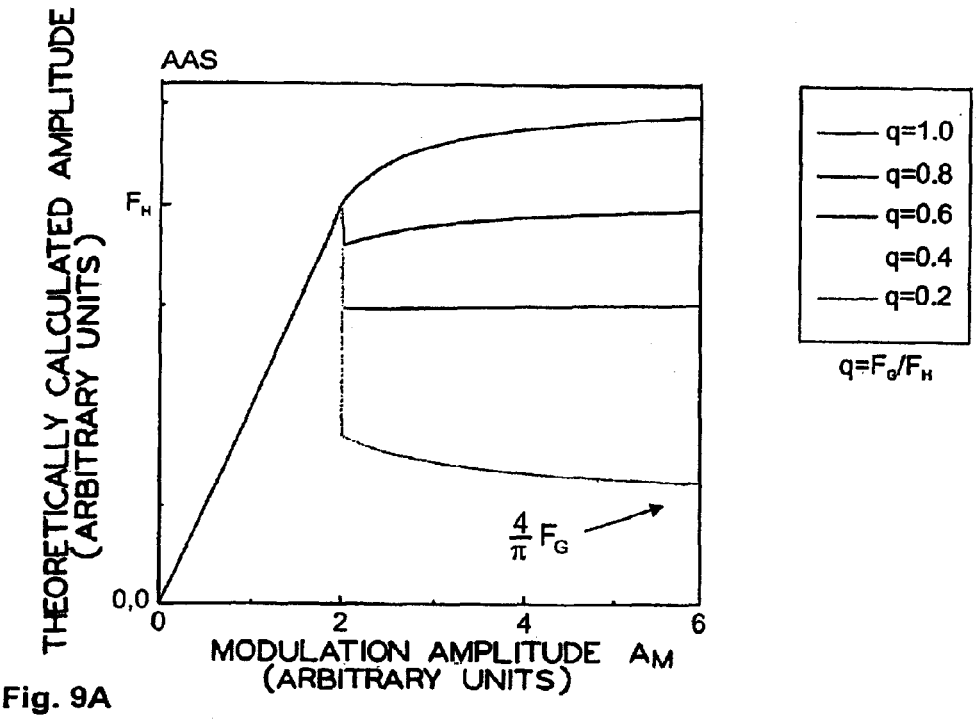
Figure 9B:
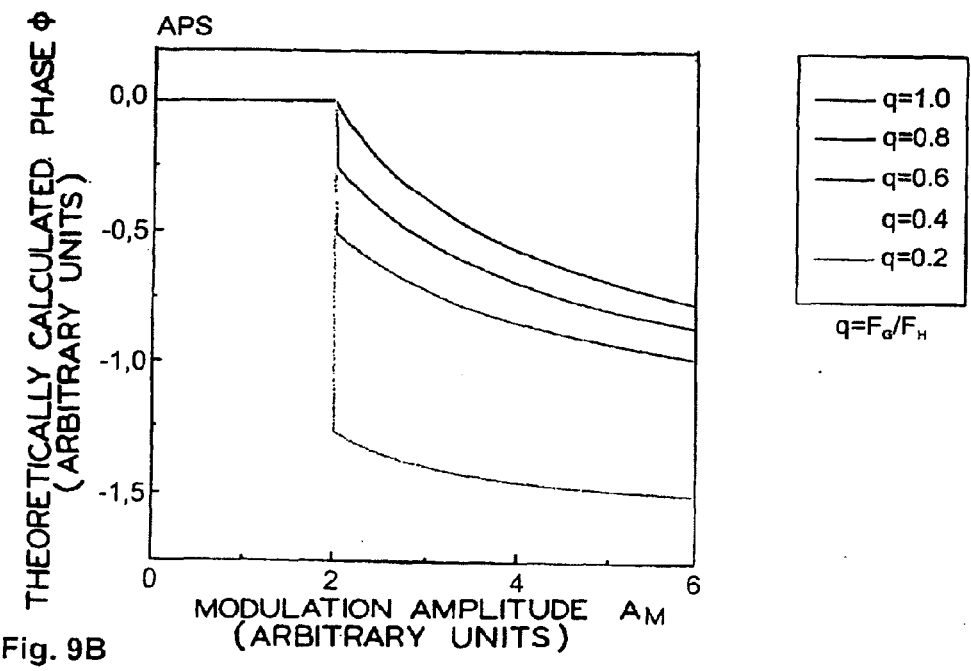
Figure 10:
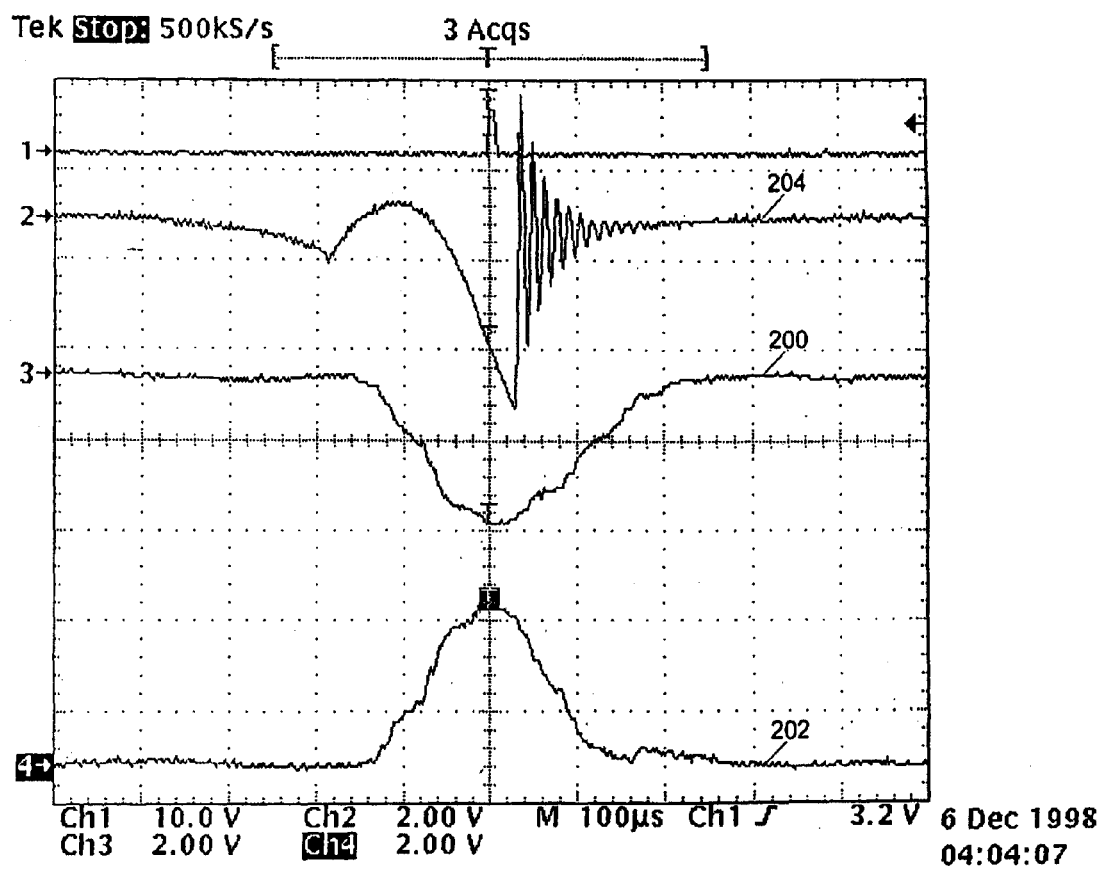
Figure 11:
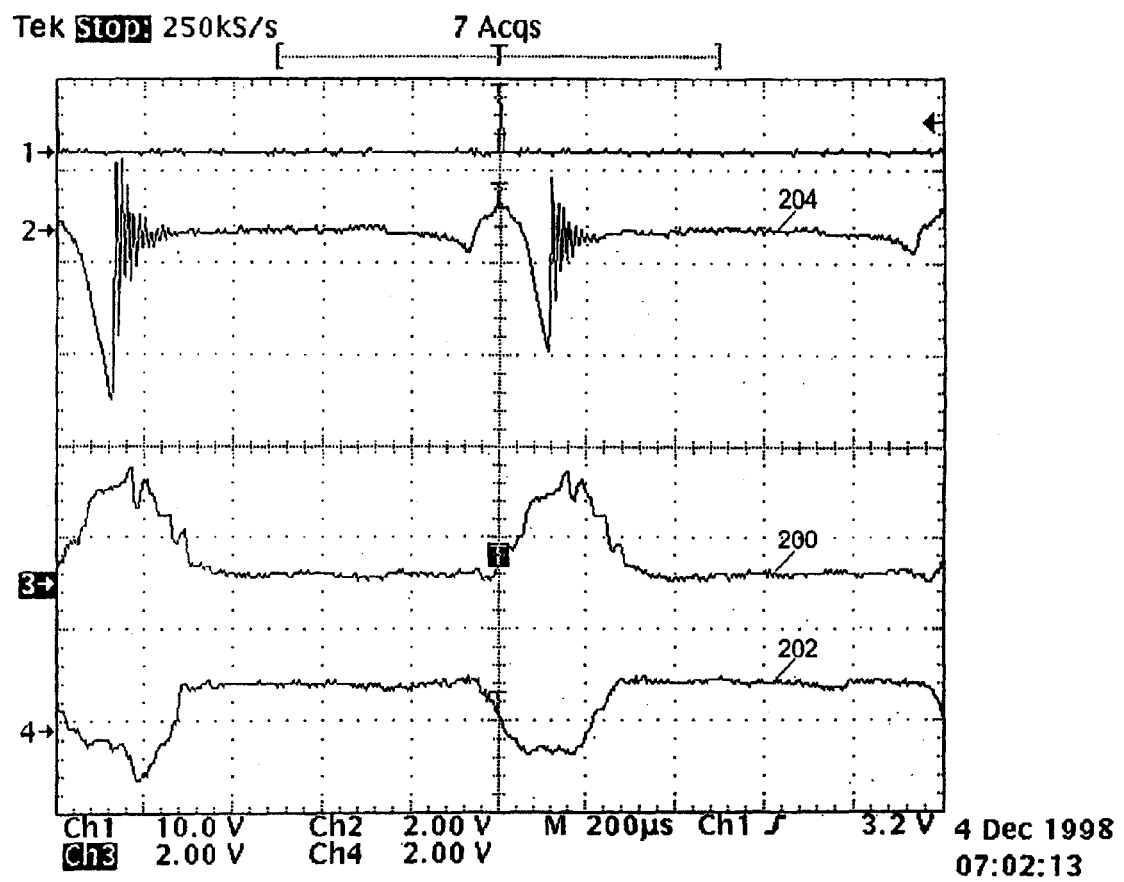
Figure 12A:
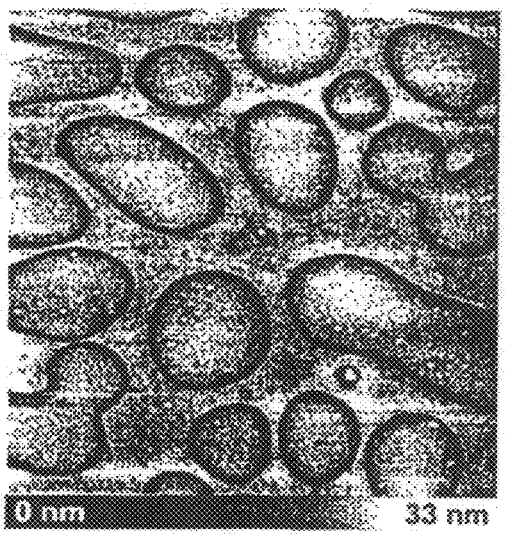
Figure 12B:
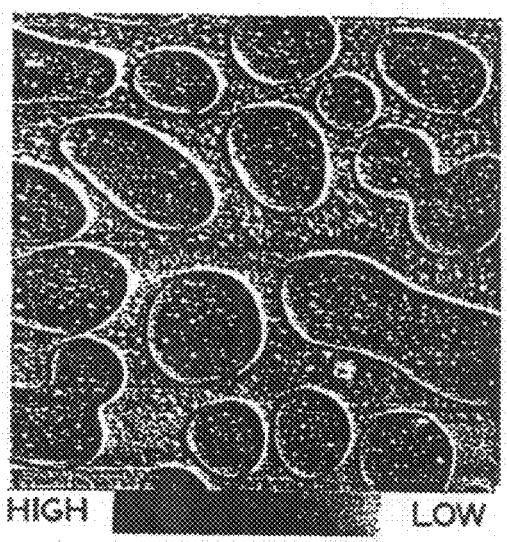
Figure 12C:
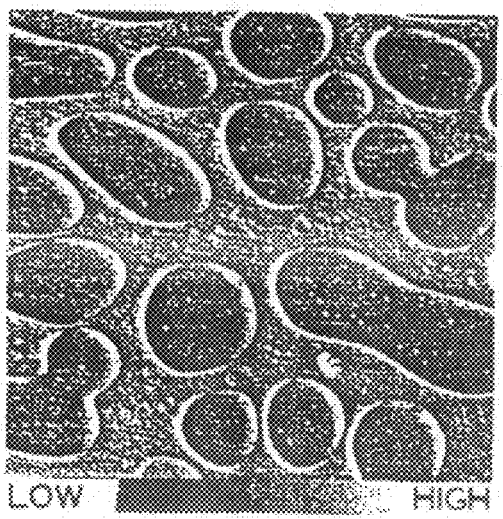
Figure 12D:
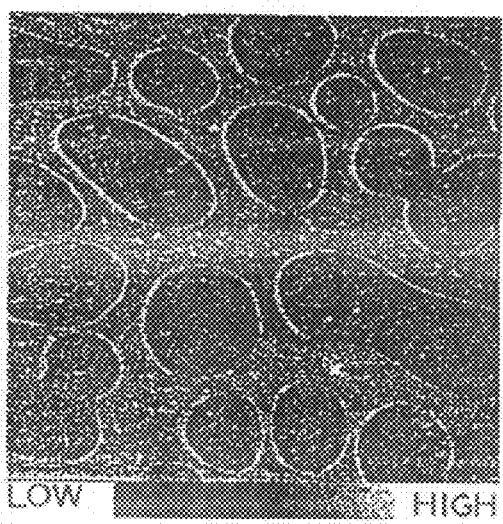
Figure 13A:
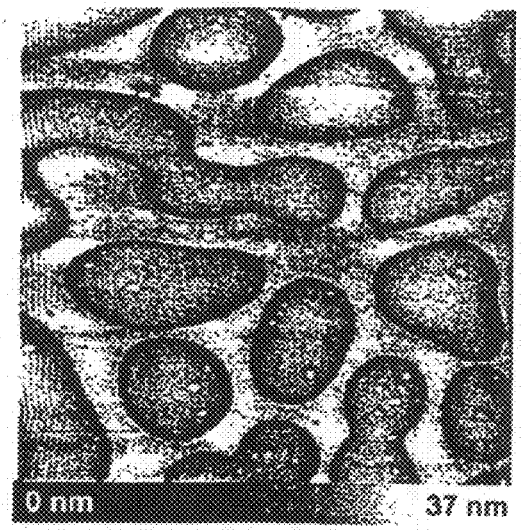
Figure 13B:
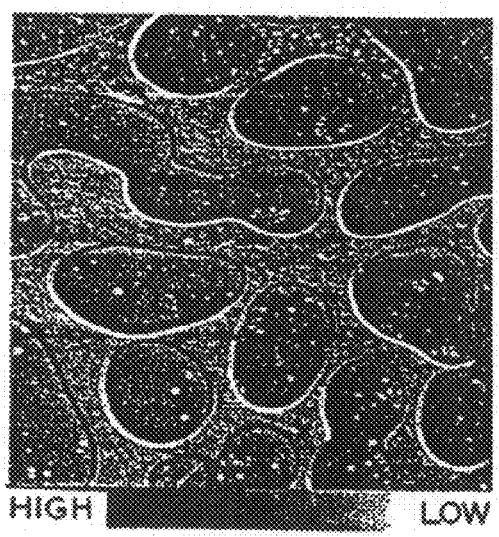
Figure 13C:
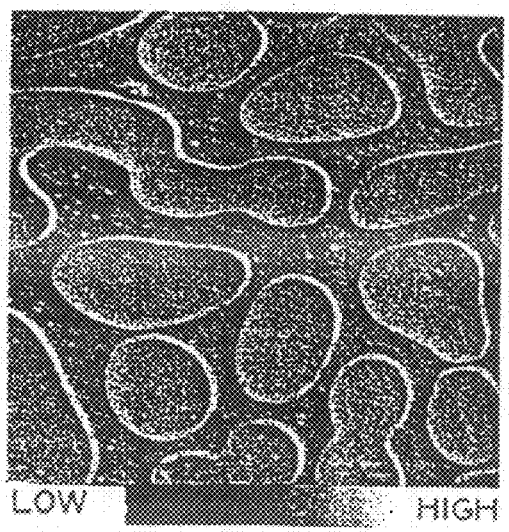
Figure 13D:
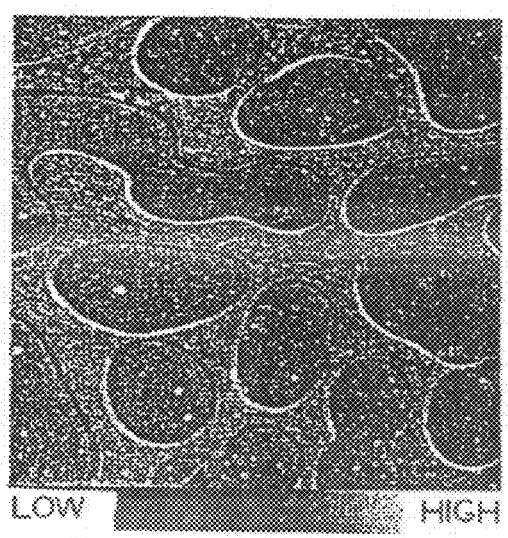

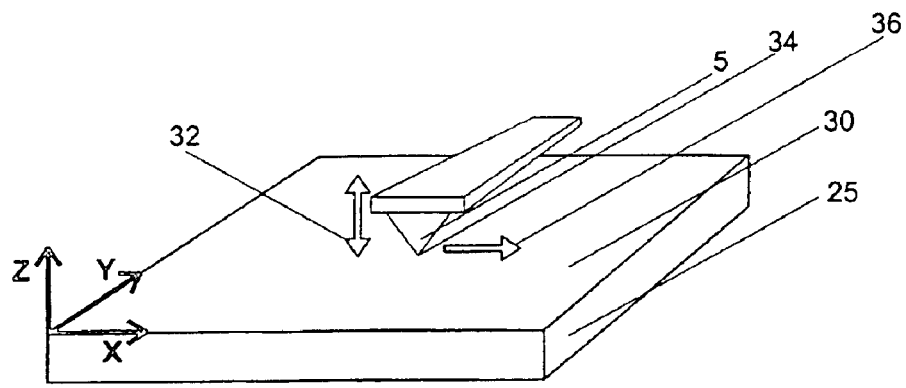
Fig. 2
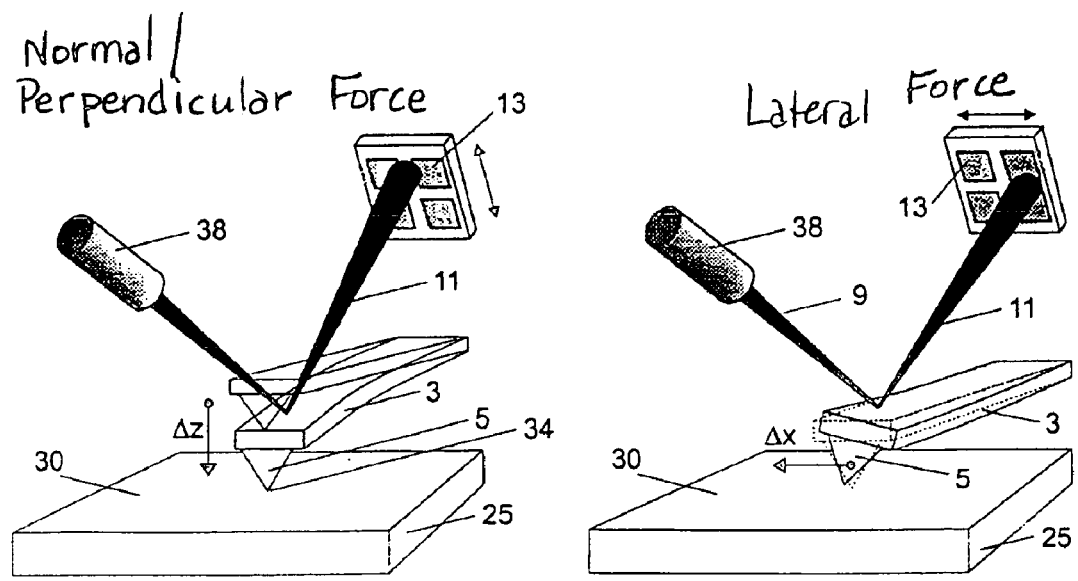
Fig. 3A
Fig. 3B

Polymer sample,
image size 25 μm²,
93kHz / 1kHz

Polymer sample,
image size 25 μm²,
230kHz / 1kHz

METHOD AND DEVICE FOR SIMULTANEOUSLY DETERMINING THE ADHESION, FRICTION, AND OTHER MATERIAL PROPERTIES OF A SAMPLE SURFACE

The present invention relates to a method for simultaneously determining at least two material properties, comprising the surface topography, the adhesion, the static and dynamic friction as well as the elasticity and rigidity, by means of a raster probe microscope comprising a raster probe. The invention relates also to an improved raster probe microscope for the carrying-out of the process according to the invention.

Raster probe microscopy makes possible the non-destructive characterization of sample surfaces on a molecular or atomic scale. Besides the topography of a surface to be examined there can also be determined a number of other surface properties, such as for example the friction, the adhesion, the yieldingness and other elastic properties.

To the class of the raster probe microscope there belong, for example, the raster tunneling microscope (STM: Scanning Tunneling Microscope), near-field microscope (SNOM: Scanning Near-Field Optical Microscope) and force or raster force microscope (SFM: Scanning Force Microscope or RKM: Raster Force Microscope).

Regarding further information on raster probe microscopy let reference be made here to the following publication of Binnig et al, Binnig, G., Quate, C. F. and Gerber, C.: Atomic Force Microscope, Phys. Reg. Lett. 930–933, 56/56 (1986).

The determination of adhesive forces occurs ordinarily over a measurement of force-distance curves by means of a raster force microscope. In such a measurement the raster probe, i.e., the test probe of the raster force microscope is moved from a relatively great distance onto the sample surface to be examined and thereupon away from it again, in which operation the distance-dependent forces are detected over the trajectory of a beam or cantilever on which the raster probe is mounted. What is disadvantageous in this manner of procedure is the very slow measuring speed, which is associated moreover with an extremely storage-intensive image recording and a very time-intensive quantitative evaluation. Moreover, such measurements are extremely subject to error. Since the force-distance curves are recorded linearly, topographic information data, furthermore, are accessible only at great cost.

Alternatively to this, adhesive forces can also be determined by a measurement in the so-called pulsed force mode (PFM). With this measuring method the surface of a sample to be examined is scanned periodically in a type of contact mode, with frequencies in the kilohertz range, preferably 0.1 to 3 kHz. By this manner of procedure there can be simultaneously determined also certain other properties of the sample, such as, for example, the local elastic rigidity and the adhesion. The adhesion values are measured on-line. The measuring of the adhesion by means of the pulsed force mode technique has the disadvantage, however, that the measuring speed must be adapted to the vertical modulation frequency and is thus subject to a restriction. With a modulation frequency of 1 kHz and an image resolution of 256 pixels there is yielded, for example, a minimal measuring speed per line of 0.256 s, in order to obtain a new measurement value for each image pixel by a contact between the raster probe and the sample.

In regard to more detailed information on the pulsed force mode let there be made reference here to the following publications: S. Hild, A. Rosa. G. Volswinkler and O. Marti, "Pulsed Force Mode—a new method for the simultaneous imaging of mechanical and chemical surface properties,", Bull. Mc. Soc. Can., 26, 24 (1998) and A. Rosa, E. Weilandt. O. Marti and S. Hild: "The simultaneous measurements of elastic, electrostatic and adhesive properties by scanning force microscopy: pulsed-force mode operation,", Meas. Sci. Technolg., 8, 1333–1338 (1997).

Besides the measurement of adhesion forces, with the aid of force microscopy friction measurements can also be carried out. The friction measurements occur ordinarily in the contact mode (SFFM: Scanning Friction Force Microscopy), in which the lateral torsion of the spring beam or cantilever is detected and used as measure for the local friction. This conventional type of friction measurement suffers from a low reproducibility of the measurment results. Since in the detected friction signals there are also contained topography effects, furthermore, no qualitative on-line results are obtained. For the ascertaining of the undesired topography effects, especially in the case of non-linearized scan-piezo elements, a time-consuming image processing is necessary in order to bring scanning images back-and-forth into coverage. The results obtained, moreover, cannot flow directly into the subsequent measurements. Furthermore, so far there are no uniform calibration standards for the quantitative determination of the friction contrasts. With the SFFM process, furthermore, only the sliding friction is measurable, so that it does not make possible any statement about the adhesion or static friction. For the exact determination of the sliding friction in dependence on the normal or perpendicular force, a measurement series with varying normal forces is necessary. Moreover, also a possible alteration or damaging of soft shearing force-sensitive samples is possible. A carrying-along of sample contaminations can lead to false friction contrasts. Furthermore, sticky sample systems are likewise not measurable.

Further information on conventional friction force microscopy can be gained, for example, from the following publications: Mate, C. M.; McCelland, G. M.; Erlandson R.; Chiang S.: Atomic-Scale Friction of a Tungsten tip on a Graphite surface, Phys. Rev. Lett. 59, (1987), 1942; Marti, O.; Colcerho, J.; Mylnek, J.; Combined scanning force and friction microscopy of mica, Nanotechnology 1, (1990), 141–144; Meyer, G., Amer, N. M. Simultaneous measurement of lateral and normal or perpendicular forces with an optical-beam-deflection atomic force microscope, Appl. Phys. Lett., (1990), 2098.

In a relatively new process for the determination of friction by means of a raster probe microscope, the sample to be examined—in addition to a conventional friction measurement in the contact mode (SFFM)—is periodically modulated laterally by means of a shearing piezo element in the 10 kHz range, perpendicularly to the slow scanning direction, in which process the torsion (Tordierung) of the spring beam in the contact mode is recorded by means of the lock-in technique, and from the measurements present there is determined the adhesion and slide friction. Besides, the topography there can be determined also still further mechanical properties, such as the elastic behavior, the (shearing) rigidity and certain relaxation times. For the exact determination of the adhesion and slide friction in dependence on the normal or perpendicular force, however, a measuring series with varying normal forces is necessary. Moreover, a possible alteration or damaging of soft shearing-force-sensitive samples is possible. Furthermore, a carrying along of sample contaminations can lead to wrong friction contacts. Furthermore, with this, too, sticky sample systems are not measurable at all or are measurable only with great difficulty.

Further information on this dynamic friction force microscopy can be gained, for example, form the following two literature references: Yamanaka, K. and Tomita, E: Lateral force modulation atomic force microscope for selective imaging of friction forces, Japanese Journal of Applied Physics, Part 1 (Regular Papers & Short Notes), vol. 34, No. 5B, pages 2879–2882, (May 1955): Yamanaka, K., Takano, H.; Tomita, E. and Fujihira, M.: Lateral force modulation atomic force microscopy of Langmuir-Blodgett film in water, Japanese Journal of Applied Physics, Part 1 (Regular Papers, Short Notes & Review Papers), vol. 35, No. 10, pages 5421–5425 (October 1996).

In the interest of completeness let there also be made reference to the post-published EP 0 896 201 A1, which discloses a raster probe microscope which comprises in addition to a raster probe also a separate detector probe for the detection of the raster probe deflection and for the control of the raster probe distance with respect to a sample surface to be examined. Here the distance dependence of the resonance behavior of the detector probe is used in a vibration excitation of the detector probe and/or of the raster probe by means of an allocated piezoelecric oscillation arrangement.

A raster probe microscope according to the generic term of claim 1 is known from the publication "Design and calibration of a scanning force microscope for friction, adhesion, and contact potential studies" by Kolestke et al. (Rev. Sci. Instrum., American Institute of Physics, New York (Jan. 9, 1995), 66(9), 4566–4574).

A locally resolved simultaneous measurement of the adhesion forces and of the friction forces and (of further mechanical sample properties) on the surface of a sample to be examined, is not made possible, however, by any of the measuring processes known from the state of the art. With a single conventional raster force microscopy measurement there can be determined either the adhesion or the friction of the sample to be examined. The determination of both these magnitudes by a single measurement with a raster force microscope has hitherto not yet been technically possible.

The problem of the present invention lies, therefore, in the creation of an improved raster probe measuring process, with which at least the adhesion and the friction can be measured simultaneously. The magnitudes mentioned should also be measurable here according to possibility, be it alone or in common, with still other properties of interest, such as, for example, certain elastic constants, comprising the adhesion and the rigidity, and/or the topography, in which context the expression "material properties" in the scope of the present specification can cover also optical signals of a sample to be examined, as well as magnetic or electric forces, information data about the temperature distribution and possibly also other measurement values. The problem consists, further, in the creation of a suitable raster probe microscope for the execution of such a measuring process.

This problem is solved according to the invention by a process in which the raster probe of a raster-probe microscope and/or the sample with the sample surface to be examined is/are moved in vertical and/or horizontal direction so that the raster probe at a pre-determined point of the sample surface interacts in a given manner with the sample surface. The raster probe here is brought into contact preferably with a given perpendicular force with the sample surface. The raster probe and/or the sample is/are subjected to a vertical oscillation and there is recorded a vertical and/or lateral deformation of a first measuring signal characterizing the vertical and/or the lateral deformation of the raster probe. In addition, a second measuring signal is recorded characterizing the deformation of the raster probe, in which operation the raster probe and/or the sample is/are subjected to a horizontal and/or to a vertical oscillation. The two measuring signals are thereupon evaluated for the determination of the desired sample properties. The first measuring signal serves here for determining the adhesion, while from the second measuring signal, in the manner still to be described in the following, the friction is determined. In order to obtain a complete information about the area of the sample surface to be examined, the raster probe and/or the sample is/are moved again, in order in the above-described manner to bring the raster probe into contact with the sample surface at the next point to be examined, at which the aforedescribed measuring process is repeated. In this manner the entire surface area to be examined is scanned linearly, as is familiar to specialists in this field.

Hereby there is obtained not only a topographic image of the sample, but it is possible for the first time, with one and the same measurement, to locally determine the friction, the adhesion and certain elastic properties of a sample on a molecular level down to the atomic level. The friction can be determined here simultaneously, in dependence on diverse normal or perpendicular forces so that measuring series with varying normal or perpendicular forces are reduced to a single measurement. This is associated not only with a clearly lower burdening of the sample by a scanning but by reason of the temporally same environmental conditions (temperature, air humidity, etc., sample aging), it makes possible also a better comparability of the determined friction values. By a varying of the normal or perpendicular force it is possible to control or determine the critical normal or perpendicular force by which in the friction measuring process the sample is altered or destroyed. Moreover, also the possibly different dependence of the friction on the adhesion on approach or withdrawal of the spring beam or cantilever is experimentally accessible. By the inventive process also some systems such as, fore example, strongly adhesive or sticky polymer systems which cannot be scanned in the contact mode and are thus inaccessible or only with difficulty accessible to a conventional normal or dynamic friction measurement, can be examined for friction by the sensitive scanning of the pulsed-force mode. By the pointwise scanning, furthermore, the carrying-along of dirt is also largely avoided, so that false friction contrasts through the interaction between the raster probe and dirt are minimized.

With the inventive measuring process the raster probe and/or the sample are preferably subjected to at least a periodic oscillation, in which the oscillation or modulation direction is chosen in particular either perpendicular or parallel to the sensing or scanning direction. Let it be pointed out, however, that arbitrary oscillation directions also are conceivable. For the determination of the dynamic friction here usually the modulation is ordinarily laterally parallel to the rapid scanning direction, which leads to a bending and torsion of the cantilever. The modulation, however, can also occur parallel to the slow scanning direction, which brings about a bending oscillation of the cantilever. Moreover, analogously to the determination of the dynamic friction there can also be carried out a vertical sample modulation, i.e., parallel to the pulsed-force mode modulation, in which case, for example, over a lock-in amplifier the vertical deformation of the raster probe is evaluated (amplitude and phase displacement). Hereby statements about the mechanical behavior of the sample are possible, especially about its elasticity and rigidity.

Advantageously the raster probe and/or the sample is excited in vertical direction with a frequency of at least 10 Hz and an amplitude of at least 1 nm, the preferred frequency and amplitude range being 500 Hz to 1 kHz and 10 to 500 nm, respectively.

To the vertical oscillation of the sample and/or the probe there is preferably superimposed at least one second oscillation with a frequency of at least 1 kHz and an amplitude of at least 0.1 nm, in particular, however, with a frequency of 5 kHz to 1 Mhz and an amplitude of 1 to 10 nm. There is advantageously used a horizontal oscillation with a frequency of at least 500 Hz, in particular, however, 10 to 100 kHz, and an amplitude of at least 0.1 nm, especially, however, 1 to 30 nm.

In a preferred example of execution the second measuring signal is evaluated in the manner thoroughly to be described below by means of a lock-in amplifier by which over a Fourier transformation of the measuring signal there are determined the friction amplitude and the phase. As raster probe there is used in particular the point or tip of a force microscope and/or of an optical near-field microscope with which there can also be detected optical signals of a sample to be examined, in which context the point or tip of the force microscope and the point or tip of the optical near-field microscope can also be integrated in a common raster probe.

A raster probe microscope suited for the execution of this process according to the invention, with the features given in the generic term of claim 1, additionally also comprises according to the invention an arrangement for the vertical and/or horizontal moving of the sample, an arrangement for detecting the sample movement and an arrangement for detecting the vertical and/or lateral deformation of the raster probe. The arrangements for the moving of the raster probe or of the sample are formed here in such manner that the raster probe and the sample surface are bringable into contact or are brought into contact in such manner that they interact with one another in a determined manner, which comprises in particular a contact with a given normal or perpendicular force.

In a preferred form of execution the arrangements for moving the raster probe or the sample comprise at least one piezo element, at least one piezo element being provided preferably for each of these arrangements.

The arrangements for moving the raster probe or the sample, especially the piezo elements mentioned, are preferably periodically excited or modulated, it being already possible to learn the type of excitation or modulation from the above description of the inventive process.

The arrangement for detecting the vertical and/or lateral deformation of the raster probe may comprise, in a preferred constructive execution, a mirror applied for example by a corresponding coating to the raster probe, which mirror is designed for the deflection of an incident laser beam, the resulting deflection being able to serve as measure for the deformation of the raster probe that is present. Corresponding information can be gained, however, for example also capacitively, interferometrically or piezoelectrically.

The inventive raster probe microscope preferably comprises an evaluating arrangement for the simultaneous determination of at least two material properties, comprising the adhesion, the static and dynamic friction, the surface topography as well as the elasticity and rigidity, by evaluation of the detected deformation of the raster probe. This evaluating arrangement can comprise, in particular, a lock-in amplifier and a microcomputer for the evaluation of the lock-in signals.

The raster probe of the inventive raster probe microscope is preferably the point or tip of a force microscope and/or of an optical near-field microscope, the point or tip of the force microscope and/or the point or tip of the optical near-field microscope also being possibly integrated in a common raster probe.

Figure 1:
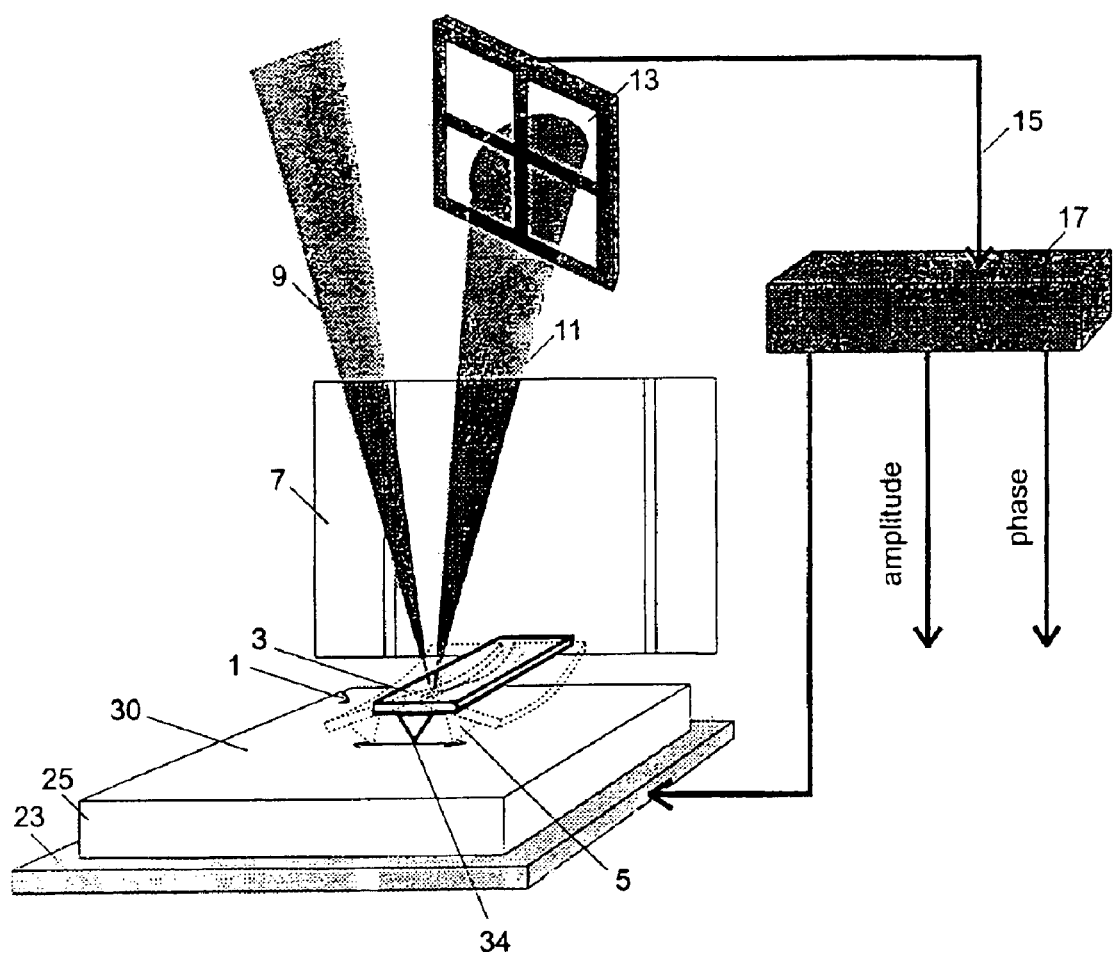
Figure 5:
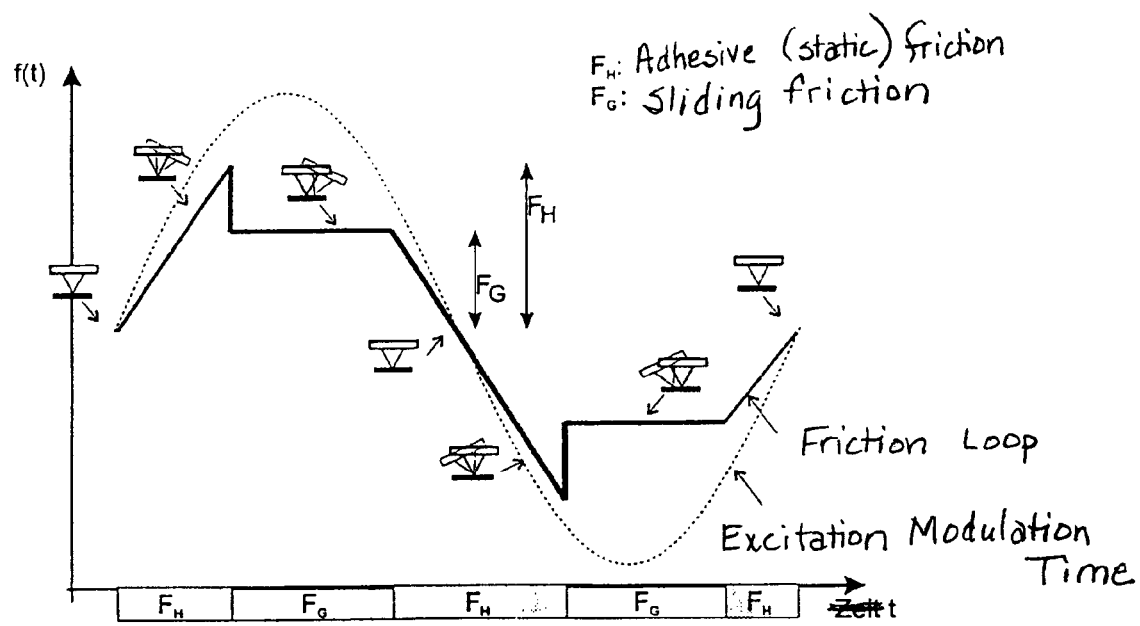
Figure 6:
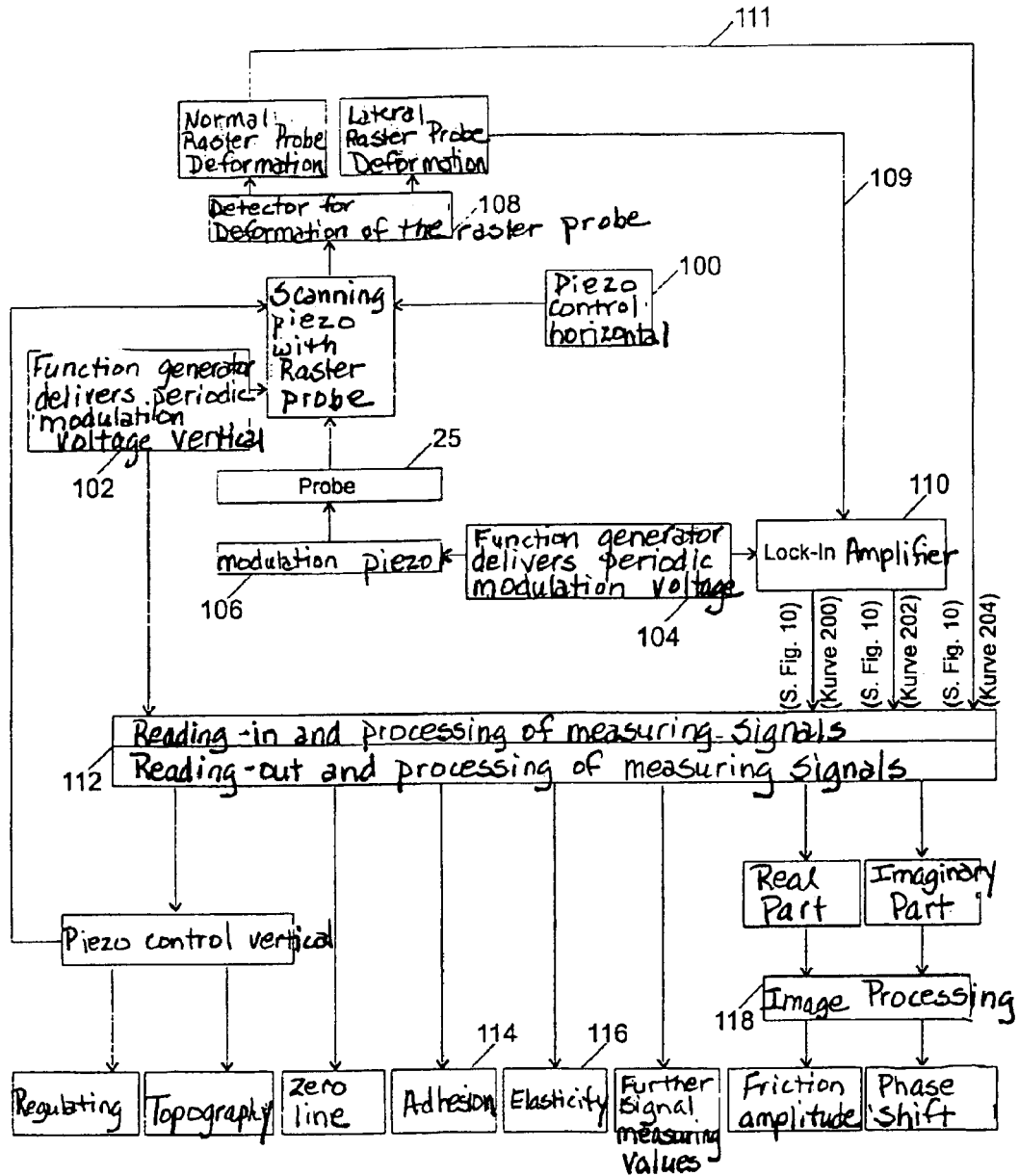
Figure 7A:
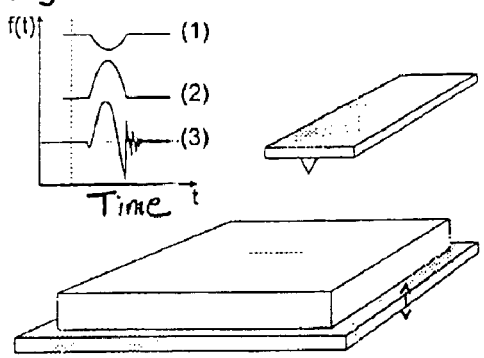
Figure 7B:
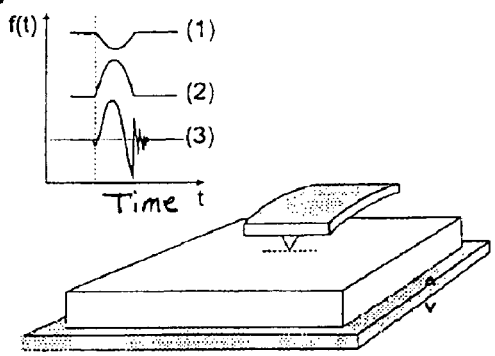
Figure 7C:
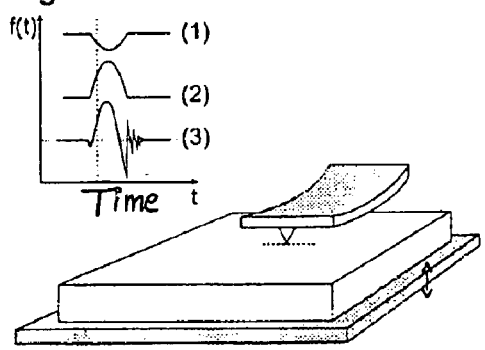
Figure 7D:
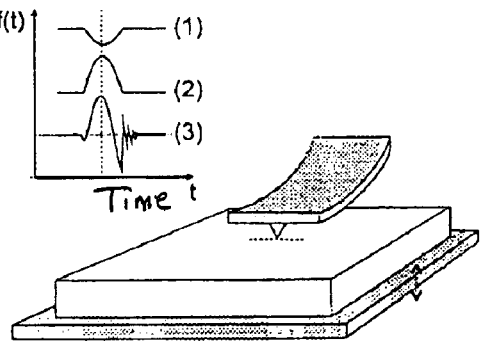
Figure 7E:
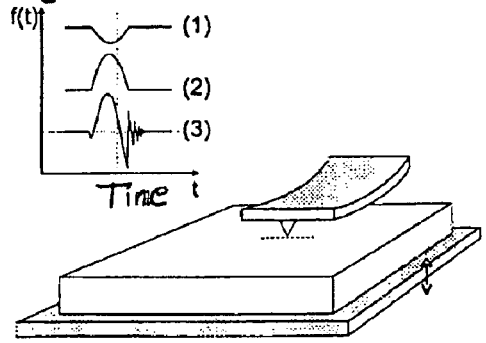
Figure 7F:
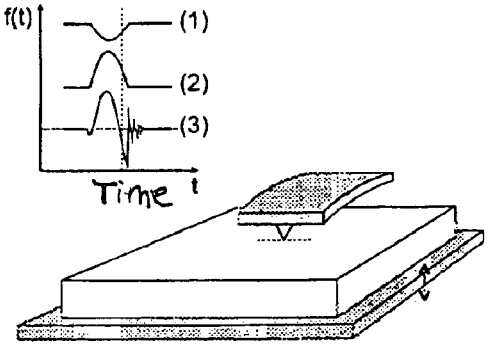
Figure 7G:
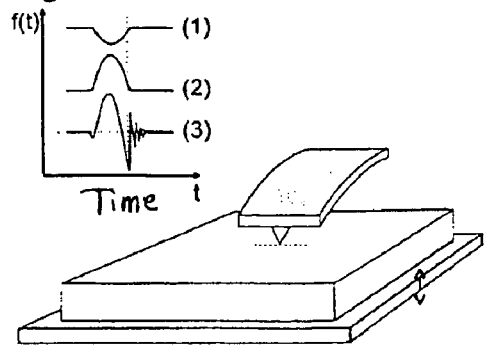
Figure 7H:
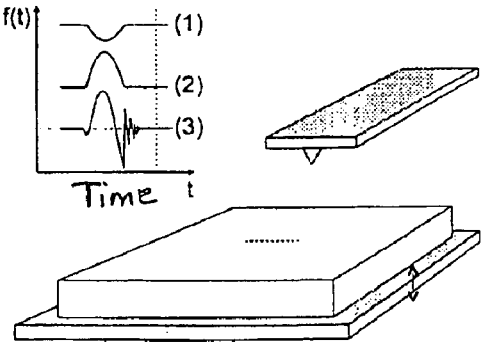
Figure 8:
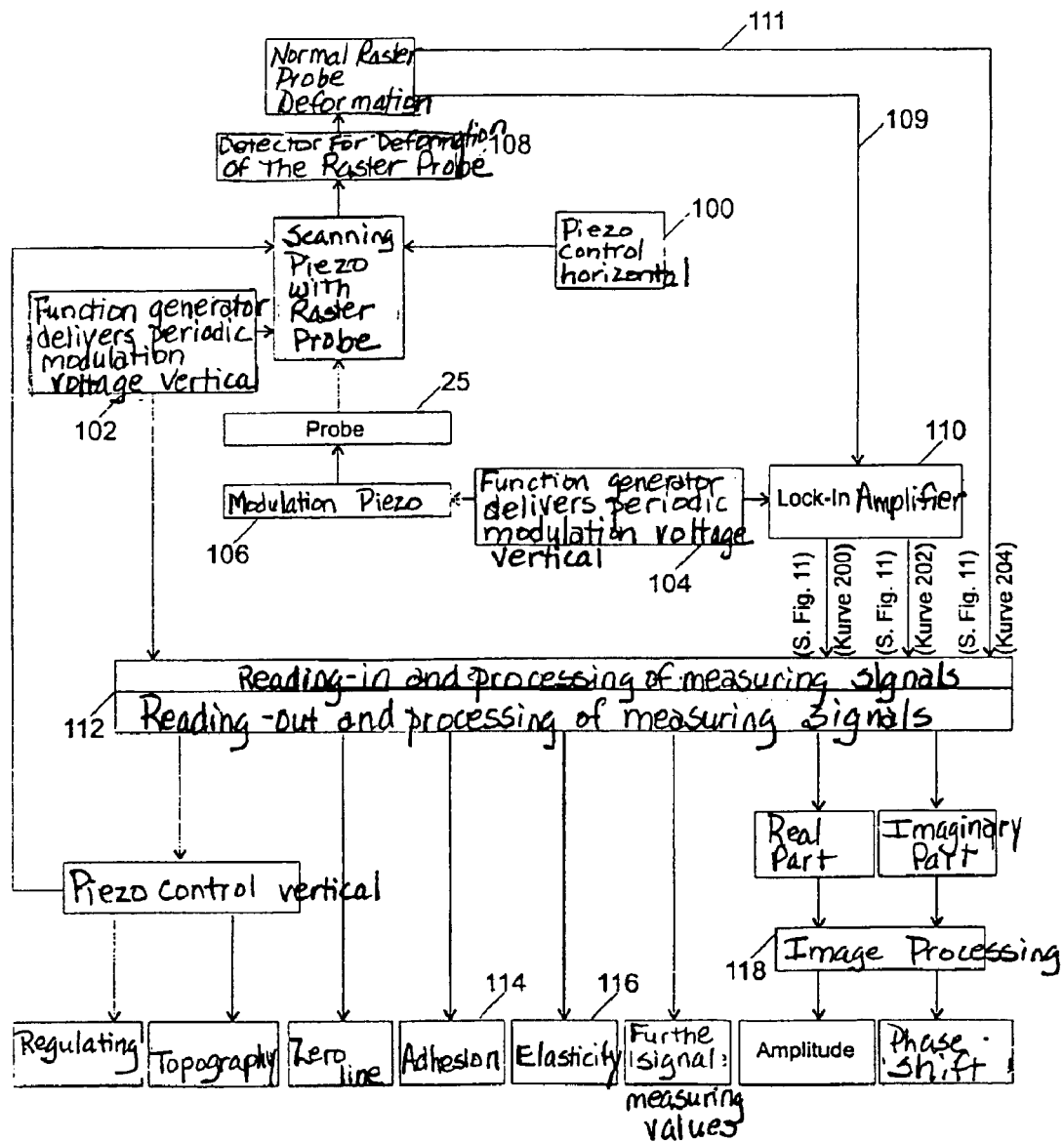
Figure 9A:
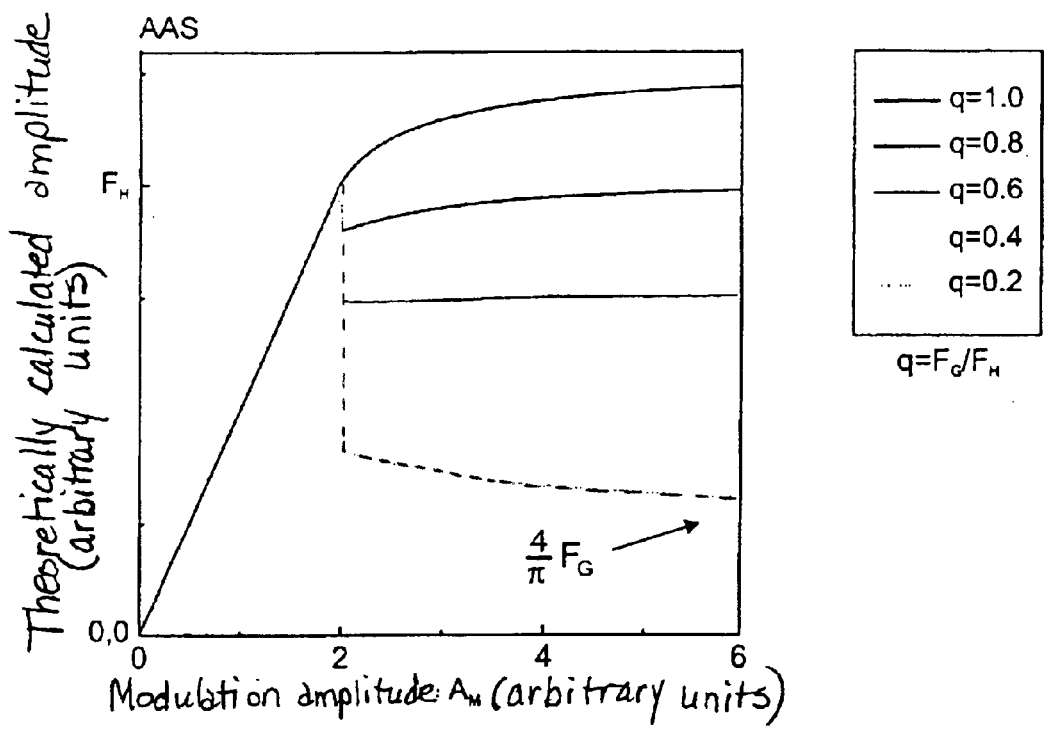
Figure 9B:
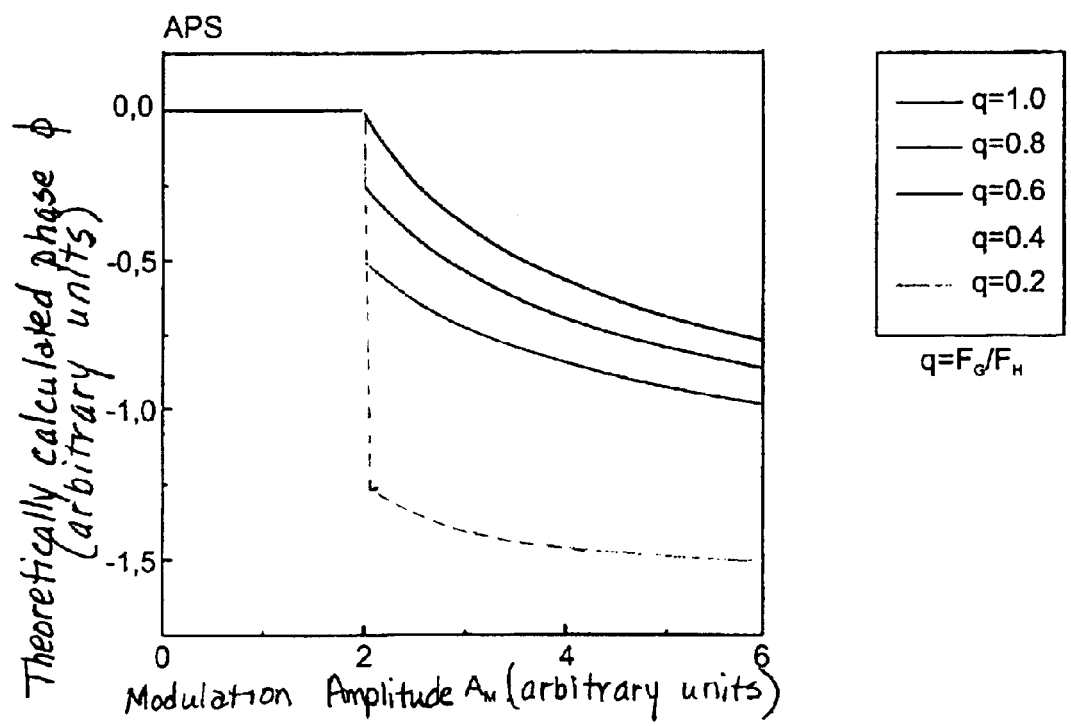
Figure 10:
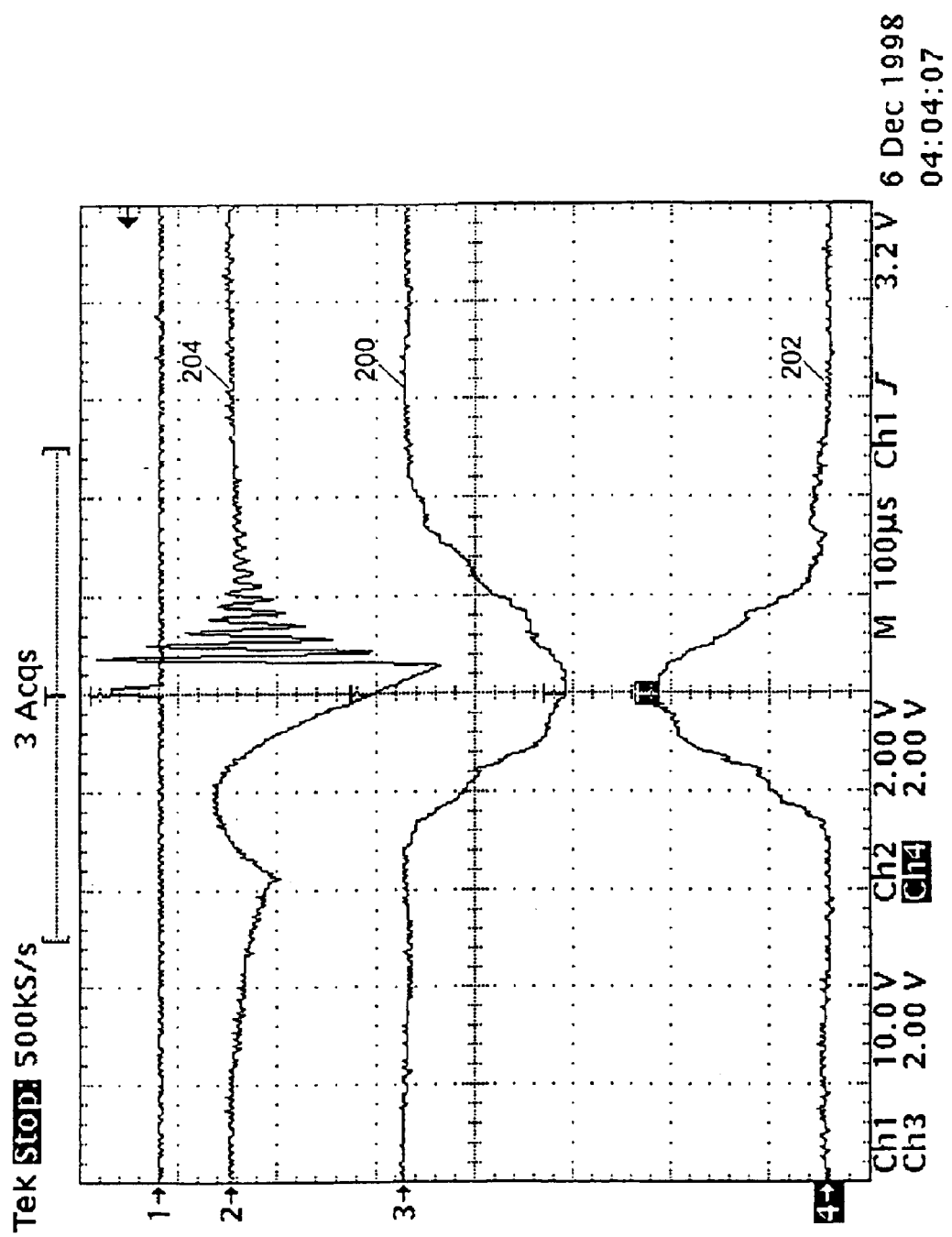
Figure 11:
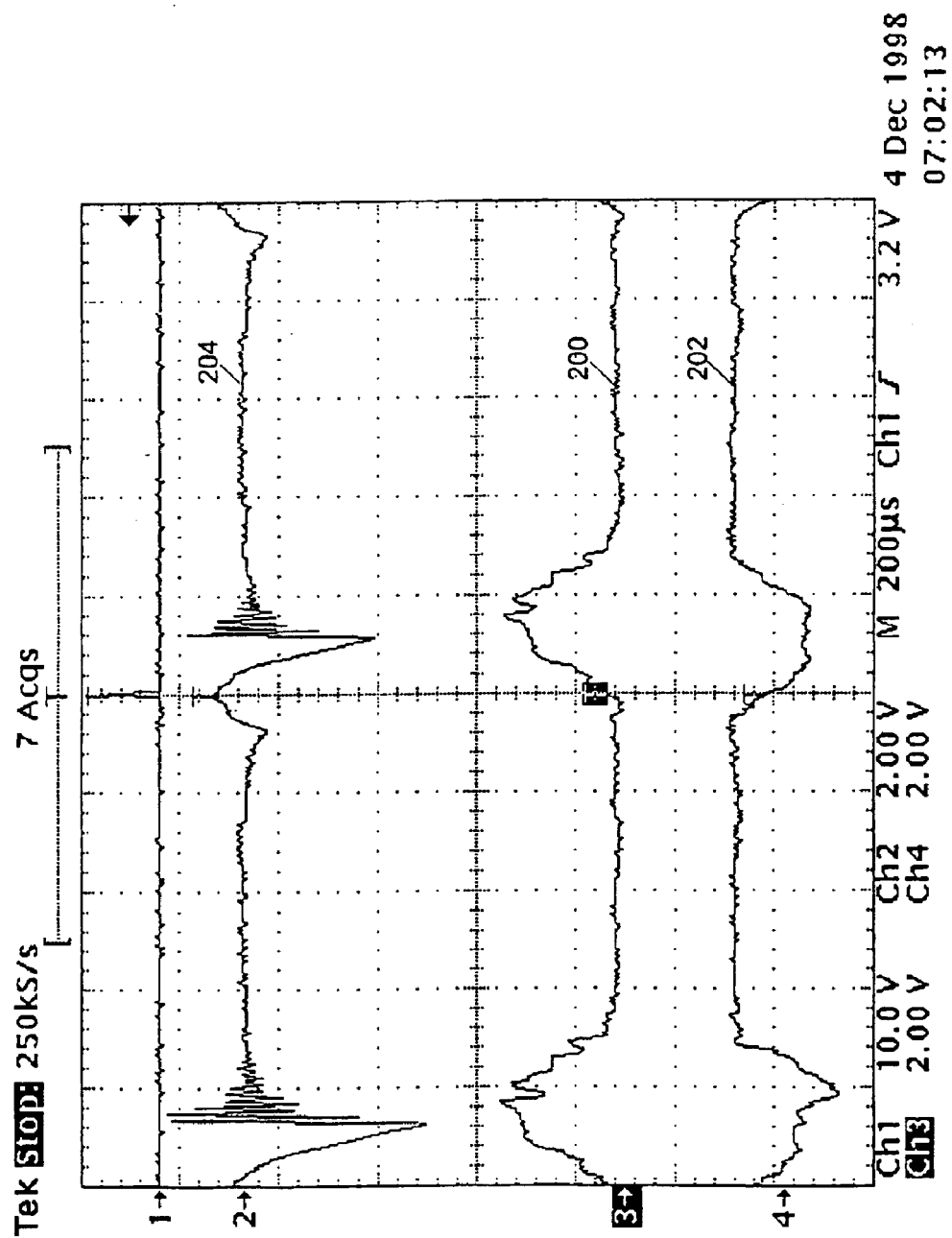
Figure 12A:
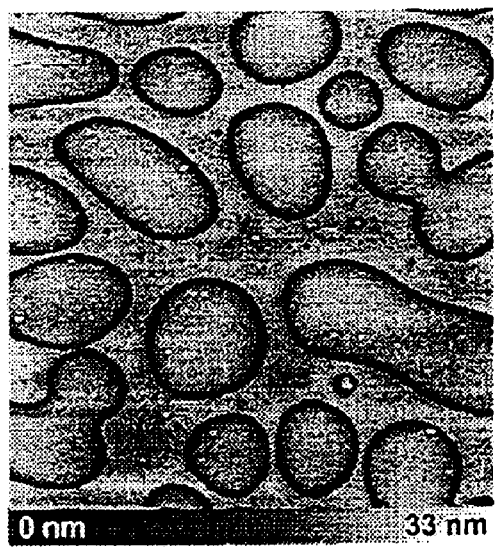
Figure 12B:
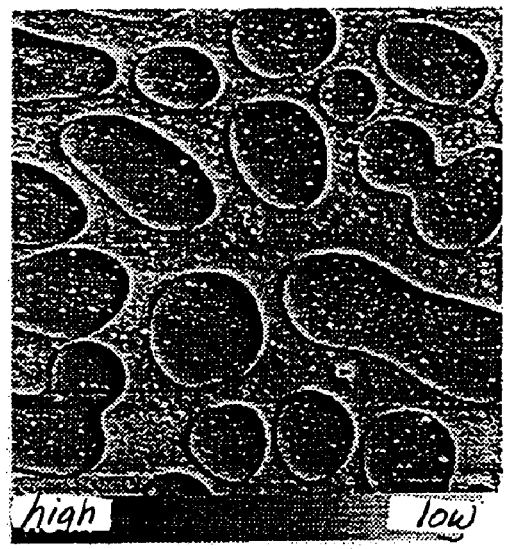
Figure 12C:
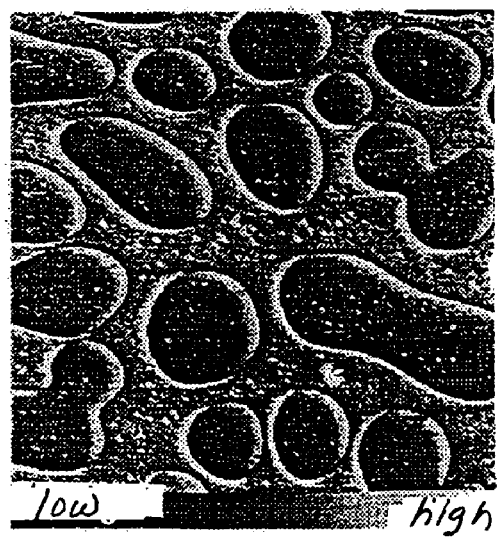
Figure 12D:
Figure 13A:
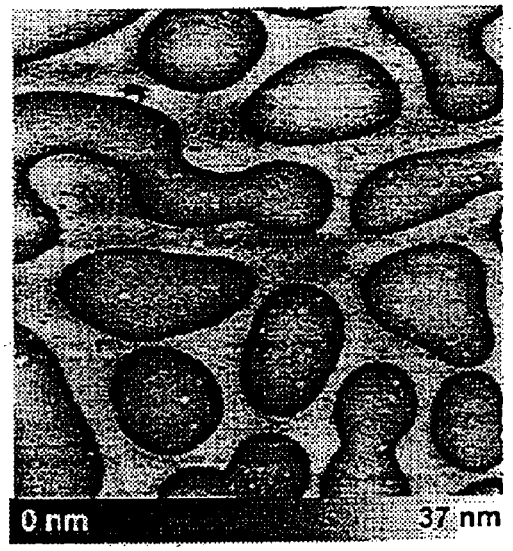
Figure 13B:
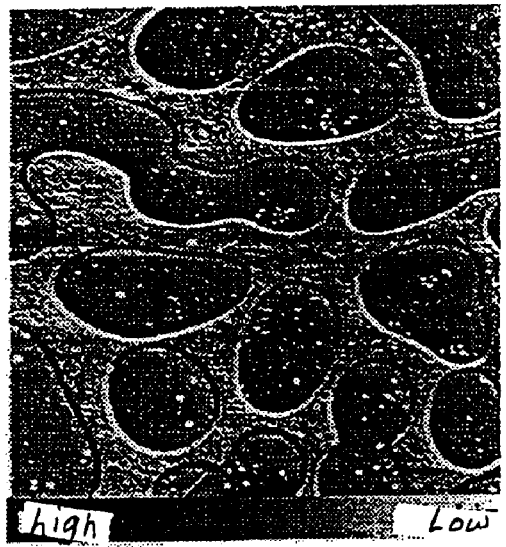
Figure 13C:
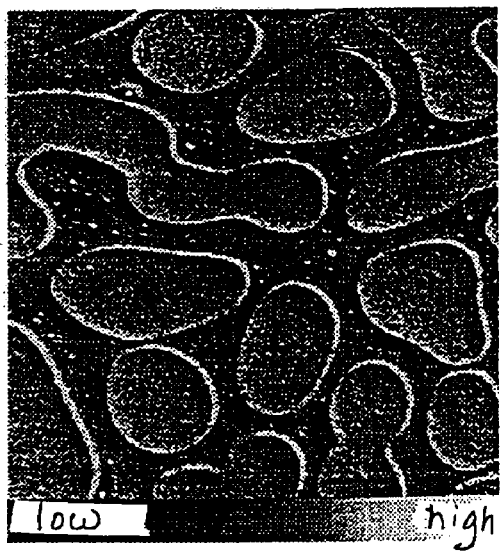
Figure 13D:
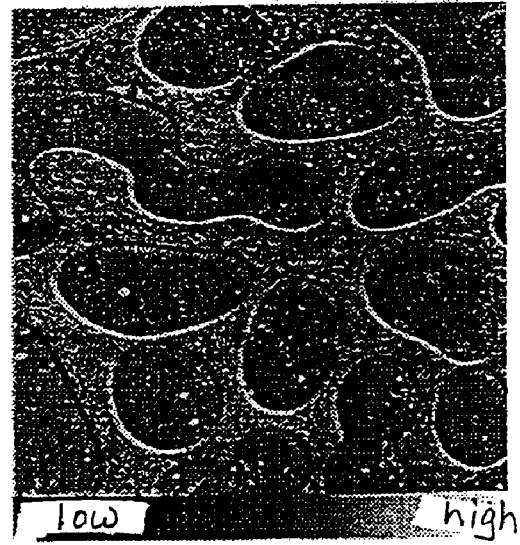

Further features and advantages of the inventive process and of the inventive raster probe microscope for the execution of this process are yielded not only from the appertaining claims—individually and/or in combination—but also from the following description of preferred examples of execution in conjunction with the appertaining drawings. In the drawings:

FIG. 1 shows the theoretical construction of a raster probe microscope according to invention;

FIG. 2 the coordinate system used as basis for the derivation of the forces;

FIG. 3A the beam bending on vertical approach to a sample surface to be examined;

FIG. 3B the beam bending in moving of the sample surface to be examined relatively to the force field peak;

FIGS. 4A to 4H the principle of a combination pulsed-force mode/dynamic friction;

FIG. 5 in schematic representation the time-dependency of a measuring signal f(t) for, the illustration of a dynamic friction measurement;

FIG. 6 a run-off diagram for a measurement according to the invention for the combination pulsed-force-mode/dynamic friction according to FIG. 4;

FIGS. 7A 7H the principle of a combination pulsed-force-mode/force modulation;

FIG. 8 a run-off diagram for a measurement according to the invention for the combination pulsed-force-mode/force modulation according to FIG. 7;

FIGS. 9A to 9B theoretically calculated friction amplitudes and phase-dependencies of the cantilever on the modulation amplitudes AM of an excitation shearing piezo element;

FIG. 10 measuring signals of the new-type raster probe microscope on the basis of a vertical bending of the cantilever (combination pulsed-force-mode/force modulation);

FIG. 11 measuring signals of the new-type raster probe microscope on the basis of a vertical bending of the cantilever (combination pulsed-force-mode/force modulation);

FIGS. 12A to 12D a depiction of the topography of the adhesion and of the friction on a sample surface, examined with a raster probe microscope according to the invention for a combination pulsed-force-mode/dynamic friction; and FIGS. 13A to 13D a depiction of the topography, the adhesion, the friction on a sample surface, examined with a raster probe microscope according to the invention for a combination pulsed-force-mode/force modulation.

The raster probe microscope represented in FIG. 1 comprises a raster probe 1 with a beam or cantilever 3 and a measuring point or tip 5. The measuring point 5 can be made, for example, of silicon or silicone nitride, for example $Si_3N_4$. The vertical shifting of the raster probe 1 is performed with the aid of a piezo element 7. The measurement of the deformation of the beam 3, which in the vertical process is a measure for the adhesion forces, is determined by means of a laser structure (not shown in detail). For this the light 9 of an unrepresented laser light source is projected onto the beam 3, from which it is reflected so that the reflected beam 11 impinges on a measuring arrangement 13, which can comprise, for example, the photosensitive layer of a segmented photo-diode.

According to the position of the beam 3 the light beam 11 is deflected upward or downward and to the left, or to the right, respectively, from the zero position shown in the drawing, and it is transformed by the photosensitive layer of the measuring arrangement 13 into an electrical signal. The electrical measuring signal yielded in a relative movement occurring in horizontal direction between the beam 3 or the measuring point or tip 5 and the sample surface 30—which according to FIG. 3B generates an essentially laterally occurring deflection of the reflected light beam 11 and is designated in the following as second measuring signal—is transmitted over a line 15 to a lock-in amplifier 17, in which a Fourier transformation is carried out and there the real part and the imaginary part of the signal are determined, from which (in a manner still to be described in the following) the desired friction can be determined. The electrical measuring signal yielded in a vertical relative movement between the measuring point or tip 5 and the sample surface 30 (the so-called first measuring signal, in which the reflected light beam according to FIG. 3A is deflected essentially upward or downward) is delivered for the determination of the adhesion over an unrepresented line,
directly to a likewise not represented evaluating arrangement 112 (see FIG. 6).

Let it be remarked that the detection of the deformation of the beam 3 by a photo-indicating principle of the type represented is only one possible type of detection, and that for specialists in this field, theoretically other possibilities of detection are also conceivable, such as, for example capacitive, interferometric or piezoelectric detection possibilities.

Besides the vertical movability, on the sample table 23 that carries the sample 25 there is arranged, according to the invention, a piezo element (not shown), with which the sample table 23 and therewith also the sample 25 can also be moved or excited laterally as was already mentioned above, for the determination of the static and dynamic friction. The measuring beam 3 of the force point or tip 5 is twisted and/or bent, as shown in broken lines, in which operation the torsion and/or .-bending arising is a measure of the friction forces present.

In FIG. 2 the coordinate system is again clarified. There is shown the measuring point or tip 5 which is moved with respect to the surface 30. A raising and lowering of the measuring point or tip 5 and/or of the sample 25 in Z-direction, as indicated with arrow 32, makes possible the adhesion measurement in the point 34; a moving or exciting in the plane of the same surface 30 along the arrow makes possible the measurement of the static and dynamic friction at the point 34 shown in the drawing.

In FIGS. 3A and 3B the resulting measuring signals are once again shown in detail. In the vertical movement in Z-direction for the measurement of the adhesion the beam 3 according to FIG. 3A is bent in Z-direction. The light beam coming from a laser 36 is reflected from the beam 3
and deflected essentially upward or downward on the measuring arrangement or measuring surface 13, the resulting deflection being a measure of the adhesion force. In FIG. 3B the measuring signal for a friction measurement is shown, in which the raster probe 1 and the sample 25 are subjected to a relative vertical movement. Again, the light beam 9 of the laser 38 is led onto the beam 3 and from this it is reflected on the measuring surface 13 essentially to the left or to the right. Since the beam 3 is twisted and/or bent by the friction of the measuring point or tip on the surface 30, the resulting deflection is a measure of the friction force.

Figure 4A:
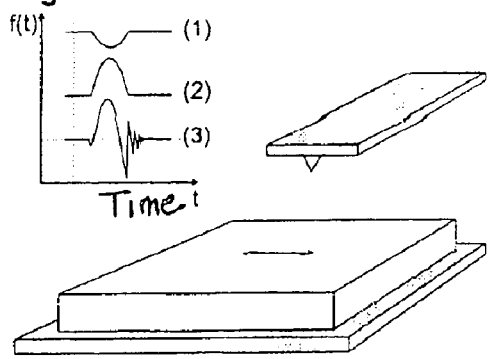

FIGS. 4A to 4H show, with the aid of a representation of the different beam or cantilever deformations during a period for the detection of the local material properties at a certain sample point, the principle of a combination pulsed-force-mode/dynamic friction, in which for better perspicuity it is only in FIG. 4A that reference numbers are given. The diagrams shown in the individual figures show here the time dependence of the detected measuring signals, in which the curves 1 and 2 correspond to the real part x and to the imaginary part y, respectively, of the second measuring signal, already mentioned above, on the basis of the lateral cantilever deformation, while the curve 3 shows a typical pulsed-force-mode force signal (first measuring signal).

In FIG. 4A the raster probe 1 is still so far remote from the sample 25 to be examined, that there is still no interaction between the raster probe 1 and the sample 25. The detected measuring signals, therefore, are equal to zero at this point in time.

Figure 4B:
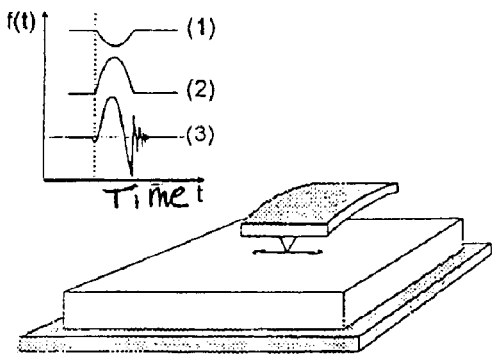

In the further approach of the raster probe 1 to the sample 25 shown in FIG. 4B, the raster probe 1 or the measuring point or tip 5, by reason of the negative (attractive) force between the raster probe 1 and the sample 25, comes in contact with the sample surface 30. This leads to a "snap-on" peak in the pulsed-force measuring signal (first measuring signal) represented in curve 3.

Figure 4C:
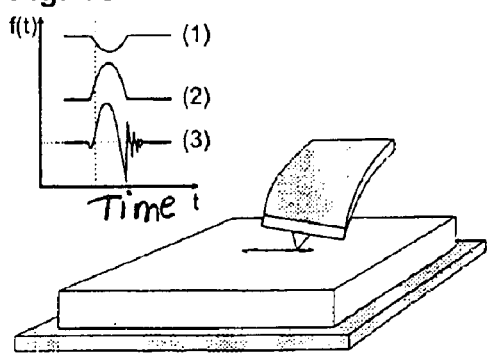

The raster probe 1 is pressed further onto the sample 25, which according to FIG. 4C leads to a rise of the first measuring signal (curve 30. Simultaneously the raster probe 1 is horizontally deformed by reason of the horizontal modulation. This leads to the detection of a second measuring signal that is represented broken down into real part and imaginary part (curves 1 and 2, respectively).

Figure 4D:
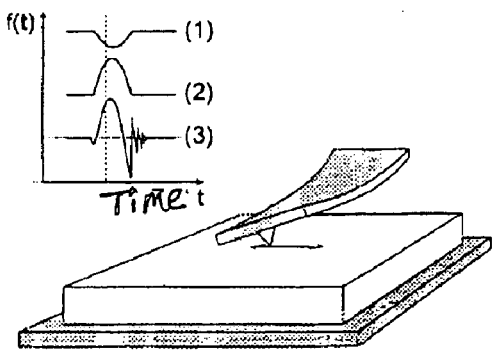

FIG. 4D illustrates how the raster probe 1 is pressed onto the sample 25 until a given normal or perpendicular force that is being registered is reached. The positive repulsive force reaches a maximum value, so that both the first measuring signal (curve 3) and also the second measuring signal (curves 1 and 2) take on a maximal value.

Figure 4E:
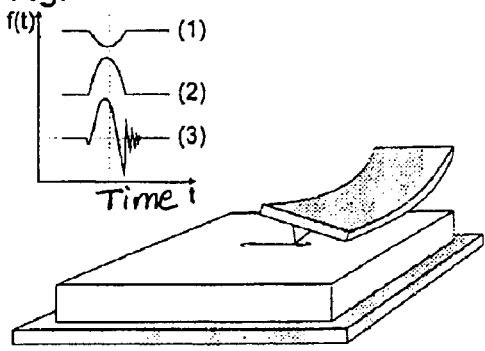
Figure 4F:
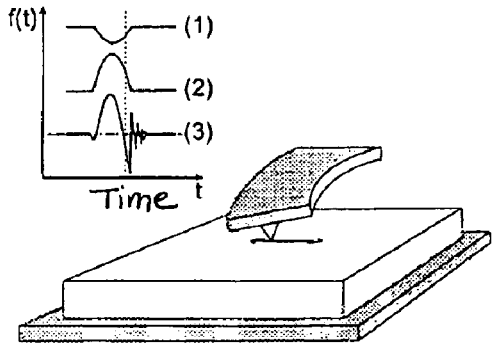

In FIG. 4E the raster probe 1 is again withdrawn from the sample 25, so that the detected measuring signals become smaller.

In a further withdrawal of the raster probe 1 from the sample surface 30 the measuring or force signals become still smaller (see FIG. 4F) and one comes again into the attractive range by reason of the adhesive interaction between the measuring point or tip 5 and the sample 25.

Figure 4G:
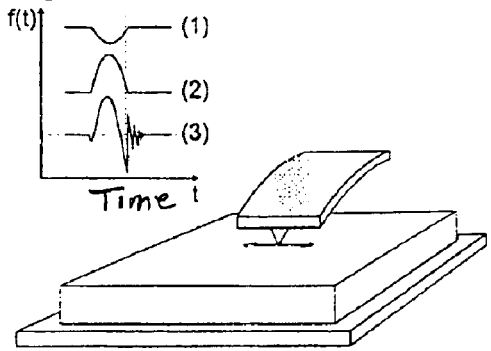

FIG. 4G illustrates how the measuring point or tip 5 still remains sticking to the sample 25 and how the negative force needed for the separation of that measuring point or tip from the sample 25, which is here designated as adhesion force, becomes maximal.

Figure 4H:
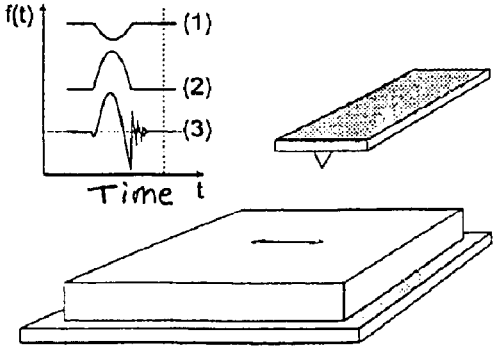

In a further withdrawal of the measuring point or tip 5 from the sample surface 30 that measuring point 5 finally comes out of contact with the sample surface 30
and swings out, which makes itself noticeable by a dying-out in the pulsed-force mode measuring signal 3 (see FIG. 4H). A new period begins.

FIG. 5 illustrates the principle of a dynamic friction measurements. In each modulation period a full friction loop is completed. At a certain deflection the measuring point or tip 5 of the force microscope can follow the excitation modulation; one finds oneself in the adhesion friction range. With a further increase of the modulation amplitude the measuring point or tip 5 of the force microscope can no longer follow the deflection and sliding friction sets in, and the detected amplitude decreases.

FIG. 6 shows a process diagram for the combination of pulsed-force mode and dynamic friction, already represented in FIG. 4, which makes possible a simultaneous measurement of the adhesion and friction or elasticity. First of all the raster probe 1 is moved with the aid of a control arrangement 100 to a predetermined sample point X, Y. Then, with the aid of a function generator 102 a periodic modulation voltage is generated which results in a periodic vertical movement of the raster probe 1 at a frequency of at least 10 Hz, especially, however, 500 Hz to 2 kHz, and an amplitude of at least 1 nm, but in particular 10 to 500 nm. In addition to the vertical periodic movement, with the aid of a function generator 104 the sample 25 is moved periodically laterally, in which process the frequency amounts to at least 500 Hz, especially 10 to 100 kHz, and the amplitude to at least 0.1 nm but in particular 1 to 30 nm. For this there is used a modulation piezo element 106. The detector arrangement 108, already represented above, which detects both the torsion (Tordierung) and/or the bending of the raster probe 1, delivers over a line 109 to a lock-in amplifier 110 the above-described second measuring signal, which is subjected to a Fourier transformation and is split into a real part x and an imaginary part y of the deformation of the raster probe.

In a likewise possible combination pulsed-force mode/ force modulation, for which a corresponding run-off diagram is shown in FIG. 8, the raster probe 1 is first moved, likewise with the aid of the control arrangement 100, onto a pre-determined sample point x,y. Then, with the aid of the function generator 102 again a periodic modulation voltage is generated, which results in a periodic vertical movement of the raster probe 1 with a frequency of at least 10 Hz, but especially 500 Hz to 2 kHz and an amplitude of at least 1 nm, but especially 10 to 500 nm. This oscillation is modulated with a second frequency of at least 1 kHz, especially 5 kHz to 1 Mhz and a second amplitude of at least 0.1 nm, especially 1 to 10 nm. The detector arrangement 108 (already mentioned above) which detects the vertical deformation of the raster probe 1, delivers over the line 109, in contra-distinction to the above process variant, the second measuring signal characterizing the vertical deformation of the raster probe 1, for the determination of the real and the imaginary parts of the measuring signal by means of a Fourier transformation.

A representation of the principle of such a measurement, analogous to FIG. 4, is to be learned from FIG. 7, wherein, however, in contra-distinction to FIG. 4 the sample 25 is modulated not laterally by vertically. Let is be pointed out that the process variants mentioned, i.e., the combination pulsed-force mode/dynamic friction and pulsed-force mode/ force modulation, are also combinable with one another.

In the above-described combination pulsed-force-mode/ dynamic friction there are calculated—from the real part and imaginary part x and y, respectively, of the detected lateral force signal, by means of an image processing arrangement 118—the friction amplitude $r=(x^2+y^2)^{1/2}$ and the phase displacement $N=\arctan(x/y)$ of the cantilever 3 with respect to the modulation amplitude of the shearing piezo element.

Corresponding dependencies are represented in FIGS. 9A and 9B. FIG. 9A shows, with the aid of the dependence of the detected amplitude on the modulation amplitude $A_M$, a resulting amplitude-amplitude spectrum (AAS), while FIG. 9B shows a resulting amplitude-phase spectrum (APS) with the dependence of the detected phase on the modulation amplitude $A_M$. For very high modulation- or excitation-amplitudes $A_M$, there holds $$\lim_{A_M \to \infty} r = 4 \cdot F_G / B$$

In the phase spectrum APS there is to be expected in the sliding friction range, according to q-factor ($q=F_G/F_H$) a clear phase displacement, in which $F_G$ is the sliding friction and $F_H$ the adhesion friction.

The friction coefficients $\mu$ are determined over $\mu = F_G/F_N$, in which the normal or perpendicular force $F_N$ is obtained from the calibrated pulsed-force-mode measuring signal on which the regulation is performed. An analogous statement holds for the APS.

If dynamic friction measurements are carried out with constant modulation amplitudes $A_M$, then to the qualitative friction and phrase contrasts by means of AAS and APS, respectively, there can be allocated quantitative friction values and phase displacements.

The recorded first measuring signals are transmitted over the line 111 directly onto the evaluating arrangement 112.

From the recorded force signals from the evaluating arrangement 112, by means of a microcomputer with a suitable computer program, there are determined also the adhesion 114 and the elasticity 116.

If this was carried out for a certain XY-point of the sample, then with the aid of the control arrangement 100 the raster probe 1 is moved to another point X, Y of the sample surface 30. At this point the previously described measurement is repeated. As was already described above, in this manner the complete sample 25 is raster-scanned, in which operation there is obtained, besides the topography, a complete picture of the adhesion, of the friction and of the elasticity on the sample surface 30.

The vertical and/or horizontal modulation can be generated not only by a shearing piezo element mounted under the sample 25 but, for example, also by a scanning piezo element.

In FIG. 10 there are shown the measuring signals detected at a pre-determined sample point on the basis of the lateral and vertical bending and/or torsion of the beam or cantilever 3, which were obtained with the process of the invention by a combination pulsed-force mode/dynamic friction. After an electronic processing and the selection of certain characteristic measuring values it is possible from these measuring signals, in the manner described, to determine the desired sample-specific properties. The curve 200 shows the real part x of a recorded second measuring signal issued from the lock-in amplifier 110, on the basis of the deformation of the cantilever, while the curve 202 represents the imaginary part of this measuring signal. The curve 204 shows the detected pulsed-force measuring signal (the measuring signal 1) on the basis of the vertical bending of the cantilever 3.

FIG. 11 shows a corresponding representation for a combination pulsed-force-mode/force modulation.

In FIG. 12 there are represented images of a sample surface 30, recorded with the inventive process, in which the horizontal excitation frequency of the sample amounts to 93 kHz and the vertical excitation frequency of the probe 1 amounts to 1 kHz. FIG. 12A shows the sample topography that is obtained from a force regulating. FIG. 12B shows the adhesion to the sample surface 30 and FIG. 12C the friction amplitude on the sample surface 30. In FIG. 12D, finally, there is shown the phase of the measuring signal.

FIG. 13 shows a corresponding representation for a combination pulse-force-mode/force modulation, in which the vertical excitation frequency of the sample is 230 kHz and the vertical excitation frequency of the probe is 1 kHz.

With the present invention there becomes available for the first time a measuring process for the simultaneous determination of the adhesion, of the friction and of further material properties, especially the elasticity and rigidity; a device is presented for the execution of this process, with the aid of which the depiction of all the sample surface is possible on the atomic scale.

A combination pulsed-force-mode/dynamic friction makes possible here especially a simultaneous measurement of the adhesion, of the friction and of other material properties, while through a combination pulsed-force-mode/force modulation besides the adhesion simultaneously still also elastic material properties and possibly also still other material properties are determinable. A combination of these two process variants makes possible even the simultaneous measurement of all the material properties mentioned.

What is claimed is:

1. A raster probe microscope for the examination of sample surfaces, comprising:
   a raster probe;
   a holding device for a sample with the sample surface to be examined;
   an arrangement for moving the raster probe and/or the sample by which the probe and sample can be brought into contact so that they interact with one another in a given manner;
   an arrangement for detecting the relative movement of the probe and sample;
   an arrangement for controlling the movement of the raster probe and/or sample and for exciting a vertical first raster probe and/or sample oscillation and for exciting at least one of a vertical and horizontal second raster probe and/or sample oscillation; and
   an arrangement for detecting at least one of a vertical and lateral deformation of the raster probe in a vertical first oscillation and at least one of a vertical and horizontal second oscillation;
   the arrangement for detecting deformation recording two measuring signals characterizing the deformation of the raster probe in a vertical first oscillation and at least one of a vertical and horizontal second oscillation of the raster probe and/or sample, and characterized by periodic raster-probe and/or sample oscillations,
   wherein the vertical oscillation of the raster probe and/or the sample occurs with a first frequency of at least 10 Hz and a first amplitude of at least 1 nm;
   wherein the vertical oscillation of the raster probe and/or of the sample is additionally excited or modulated with a second frequency of at least 1 kHz and a second amplitude of at least 0.1 nm.

2. Raster probe microscope according to claim 1, wherein the arrangement for moving the raster probe and/or the sample comprises at least one first piezo element.

3. Raster probe microscope according to claim 1, wherein the oscillation direction runs one of parallel and perpendicular to one of the sensing and scanning direction.

4. Raster probe microscope according to claim 1, wherein the first frequency is 500 Hz to 1 kHz and the amplitude is 10 to 500 nm.

5. Raster probe microscope according to claim 1, wherein the second frequency ranges from 5 kHz to 1 MHz and the second amplitude from 1 to 10 nm.

6. Raster probe microscope according to claim 1, wherein the second raster-probe and/or sample oscillation is a horizontal oscillation with a frequency of at least 500 Hz and an amplitude of at least 0.1 nm.

7. Raster probe microscope according to claim 6, wherein the horizontal oscillation frequency ranges from 10 kH to 100 kH and the horizontal oscillation amplitude from 1 to 30 nm.

8. Raster probe microscope according to claim 1 including an evaluating arrangement for the two measuring signals for the simultaneous determination of at least two material properties from the group consisting of the adhesion, the static and dynamic friction, the surface topography and the elasticity and rigidity.

9. Raster probe microscope according to claim 8, wherein the evaluating arrangement comprises one of a lock-in amplifier and a microcomputer.

10. Raster probe microscope according to claim 1, wherein the raster probe is a point or tip of one of a force microscope and an optical near-field microscope.

* * * * *

UNITED STATES PATENT AND TRADEMARK OFFICE
CERTIFICATE OF CORRECTION

PATENT NO.     : 6,880,386 B1
DATED          : April 19, 2005
INVENTOR(S)    : Hans-Ulrich Krotil et al.

It is certified that error appears in the above-identified patent and that said Letters Patent is hereby corrected as shown below:

Title page should be deleted and substitute therefor the attached title page.

Replace sheets 1 through 12, showing Figs. 1 through 13D, with attached sheets 1 through 12 showing Figs. 1 through 13D.

Signed and Sealed this

Thirteenth Day of September, 2005

JON W. DUDAS
*Director of the United States Patent and Trademark Office*

(12) United States Patent  
Krotil et al.

(10) Patent No.: US 6,880,386 B1  
(45) Date of Patent: Apr. 19, 2005

(54) METHOD AND DEVICE FOR SIMULTANEOUSLY DETERMINING THE ADHESION, FRICTION, AND OTHER MATERIAL PROPERTIES OF A SAMPLE SURFACE

(75) Inventors: Hans-Ulrich Krotil, Neu-Ulm (DE); Thomas Stifter, Illereichen (DE); Othmar Marti, Ulm (DE)

(73) Assignee: Witec Wissenschaftliche Instrumente und Technologie GmbH, Ulm (DE)

(*) Notice: Subject to any disclaimer, the term of this patent is extended or adjusted under 35 U.S.C. 154(b) by 0 days.

(21) Appl. No.: 09/869,789

(22) PCT Filed: Jan. 4, 2000

(86) PCT No.: PCT/DE00/00003

§ 371 (c)(1),  
(2), (4) Date: Jul. 23, 2002

(87) PCT Pub. No.: WO00/40946

PCT Pub. Date: Jul. 13, 2000

(30) Foreign Application Priority Data

Jan. 5, 1999 (DE) .................................. 199 00 114

(51) Int. Cl.[7] .................. G01N 13/16; G01N 19/02; G01N 19/04; G01B 11/30; G01B 21/30
(52) U.S. Cl. .................................................. 73/105
(58) Field of Search ........................ 73/105, 9, 866, 73/801; 250/306–307

(56) References Cited

U.S. PATENT DOCUMENTS

| 5,444,244 A | 8/1995 | Kirk et al. |
| 5,477,732 A | 12/1995 | Yasue et al. .................. 73/105 |
| 5,503,010 A | 4/1996 | Yamanaka |

(Continued)

FOREIGN PATENT DOCUMENTS

| DE | 44 37 081 | 4/1995 | .......... G01N/19/04 |
| DE | 9421715 U1 * | 7/1996 | .......... H02N/2/04 |
| DE | 19502822 A1 * | 8/1996 | .......... H01J/37/28 |
| DE | 197000747 A1 * | 7/1998 | .......... H01J/37/28 |
| DE | 197 28 357 | 1/1999 | .......... H01J/37/28 |
| EP | 0 611 945 | 11/1997 | .......... G01B/7/34 |
| EP | 0 896 201 A1 | 2/1999 | |
| WO | WO 00/40946 | 7/2000 | |

OTHER PUBLICATIONS

Kazushi Yamonaka et al "Lateral Force Modulation Atomic Force Microscope for Selective Imaging of Friction Forcess" *Japanese J. Apple Phys.* vol. 34, Part 1, No. 5B, pp 2879–2882, May 1995.*

(Continued)

*Primary Examiner*—Thomas P. Noland  
(74) *Attorney, Agent, or Firm*—Baker & Daniels

(57) ABSTRACT

A process for the location-resolved simultaneous detection of the adhesion and friction as well as possibly of other material properties of a sample surface to be examined by means of a raster probe microscope comprising a raster probe. The raster probe and/or the sample with sample surface are moved until at a point of the sample surface to be examined the raster probe interacts in a determined manner with this surface. The raster probe and/or the sample are subjected to a vertical oscillation, and a first measuring signal characterized by the deformation of the raster probe is recorded. A second measuring signal characterizing the deformation of the raster probe is recorded, wherein the raster probe and/or the sample are subjected to a horizontal and/or vertical oscillation. From these two measuring signals the desired material properties are determined. For the detection of the entire surface area to be examined the raster probe and or the sample are again moved and for the repetition of the measuring process described brought into contact with the sample surface in the above described manner.

10 Claims, 12 Drawing Sheets

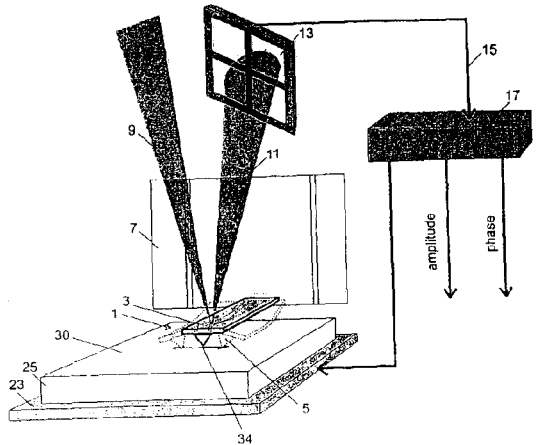

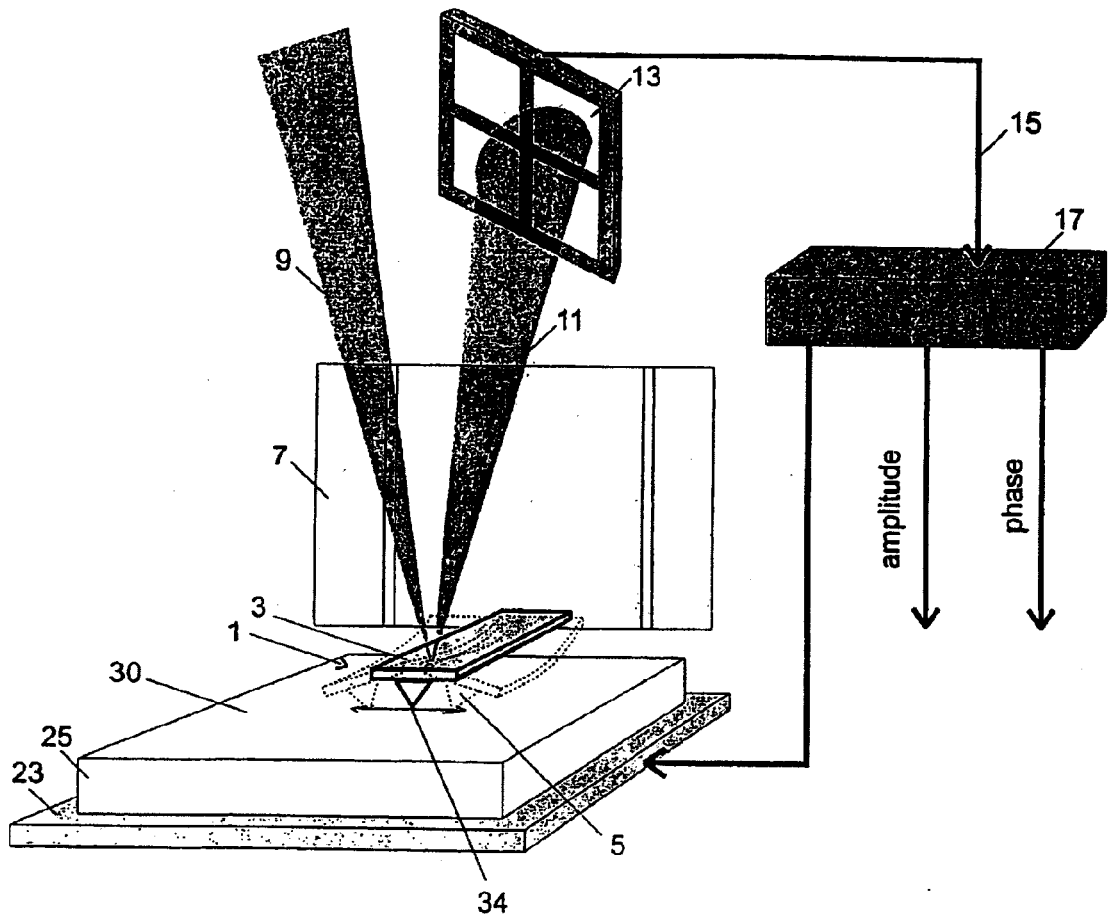

POLYMER SAMPLE,
IMAGE SIZE 25 μm²;
230kHz / 1kHz